(12) United States Patent
Ryu et al.

(10) Patent No.: US 11,801,362 B2
(45) Date of Patent: Oct. 31, 2023

(54) SURGICAL CANNULAS AND RELATED METHODS

(71) Applicant: The Texas A&M University System, College Station, TX (US)

(72) Inventors: Seok Chang Ryu, College Station, TX (US); Rohith Karthikeyan, College Station, TX (US); Shivanand Pattanshetti, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 1198 days.

(21) Appl. No.: 16/418,429

(22) Filed: May 21, 2019

(65) Prior Publication Data

US 2019/0351180 A1    Nov. 21, 2019

Related U.S. Application Data

(60) Provisional application No. 62/674,281, filed on May 21, 2018.

(51) Int. Cl.
*A61M 25/00* (2006.01)
*A61B 17/00* (2006.01)
(Continued)

(52) U.S. Cl.
CPC ... *A61M 25/0013* (2013.01); *A61B 17/00234* (2013.01); *A61B 34/20* (2016.02); *B23K 26/382* (2015.10); *A61B 17/3478* (2013.01); *A61B 2017/00309* (2013.01); *A61B 2017/00314* (2013.01); *A61B 2017/00323* (2013.01);
(Continued)

(58) Field of Classification Search
CPC .......... A61M 25/0013; A61M 25/0054; A61M 2207/10; A61M 25/0138; A61M 25/0147; A61M 2025/0166; A61B 17/00234; A61B 34/20; A61B 17/3478; A61B 2017/00309; A61B 2017/00314; A61B 2017/00323; A61B 2017/00526; A61B 2034/2061; A61B 17/3421; A61B 90/361; A61B 2017/2901; A61B 2017/3445; A61B 2562/0266; B23K 26/382; B23K 26/38; B23K 26/40; B23K 2101/06;
(Continued)

(56) References Cited

U.S. PATENT DOCUMENTS 5,507,751 A * 4/1996 Goode ................... A61N 1/057
                                                            606/108
2004/0138525 A1* 7/2004 Saadat ................. A61B 1/0055
                                                            600/104

(Continued)

*Primary Examiner* — Richard G Louis
(74) *Attorney, Agent, or Firm* — CONLEY ROSE, P.C.

(57) ABSTRACT

Embodiments disclosed herein are directed to surgical cannulas and methods relating thereto. In some embodiments, a method includes cutting one or more lines in a tubular member to form a tubular body and a hinge of a surgical cannula. In some embodiments, a surgical cannula includes a fiber brag grating (FBG) reflector mounted to a tendon for deflecting a distal tip of the surgical cannula. A controller is coupled to the FBG reflector and is configured to determine a tension in the tendon based on reflected light from the FBG reflector. In some embodiments, a surgical cannula includes a tubular body including a plurality of apertures extending therethrough.

9 Claims, 15 Drawing Sheets

(51) Int. Cl.
  *A61B 34/20* (2016.01)
  *B23K 26/382* (2014.01)
  *A61B 17/34* (2006.01)

(52) U.S. Cl.
  CPC ............... *A61B 2017/00526* (2013.01); *A61B 2034/2061* (2016.02); *A61M 25/0054* (2013.01); *A61M 2207/10* (2013.01)

(58) Field of Classification Search
  CPC ............ B23K 2101/20; B23K 2103/14; B23K 2103/26; G01L 1/246
  See application file for complete search history.

(56) References Cited

U.S. PATENT DOCUMENTS

| | | | |
|---|---|---|---|
| 2004/0193015 A1* | 9/2004 | Ikeda ................... | A61B 1/0016 600/145 |
| 2010/0160929 A1* | 6/2010 | Rogers ................... | A61B 34/30 606/130 |
| 2012/0197097 A1* | 8/2012 | Chan ...................... | A61B 90/06 600/478 |

* cited by examiner

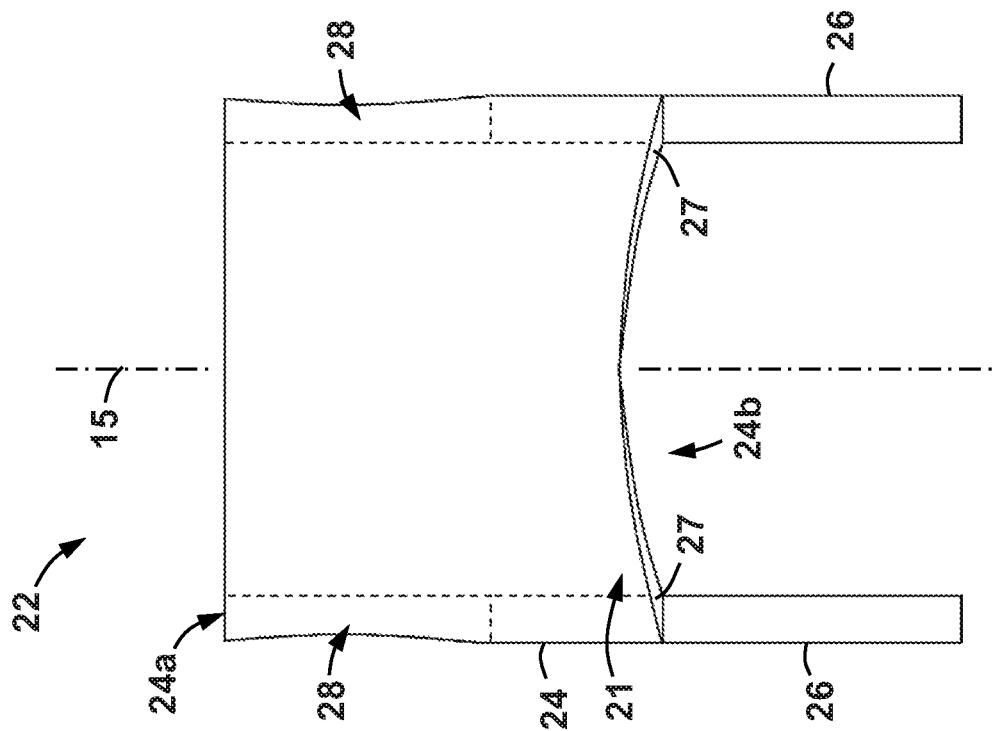
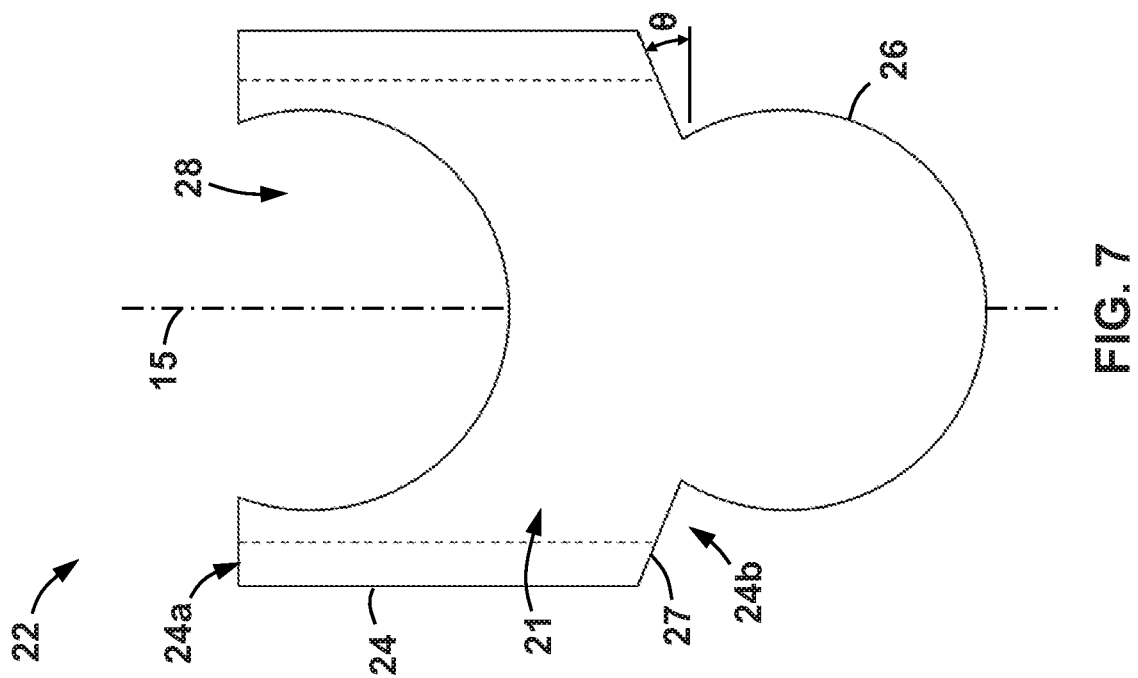

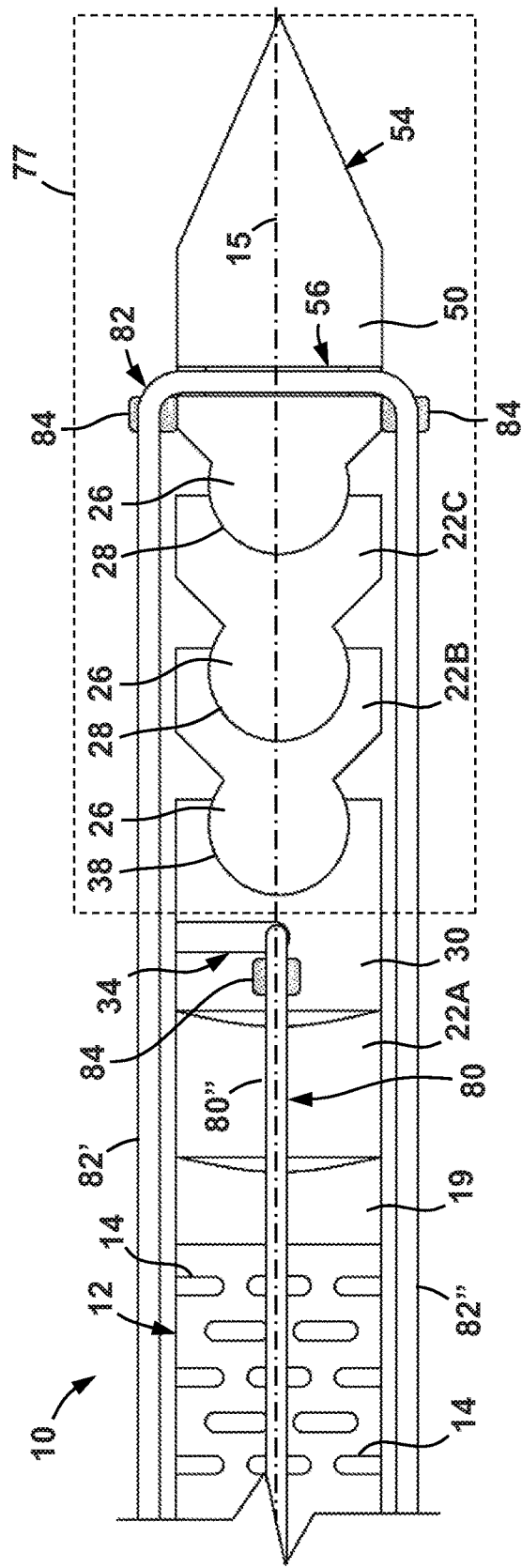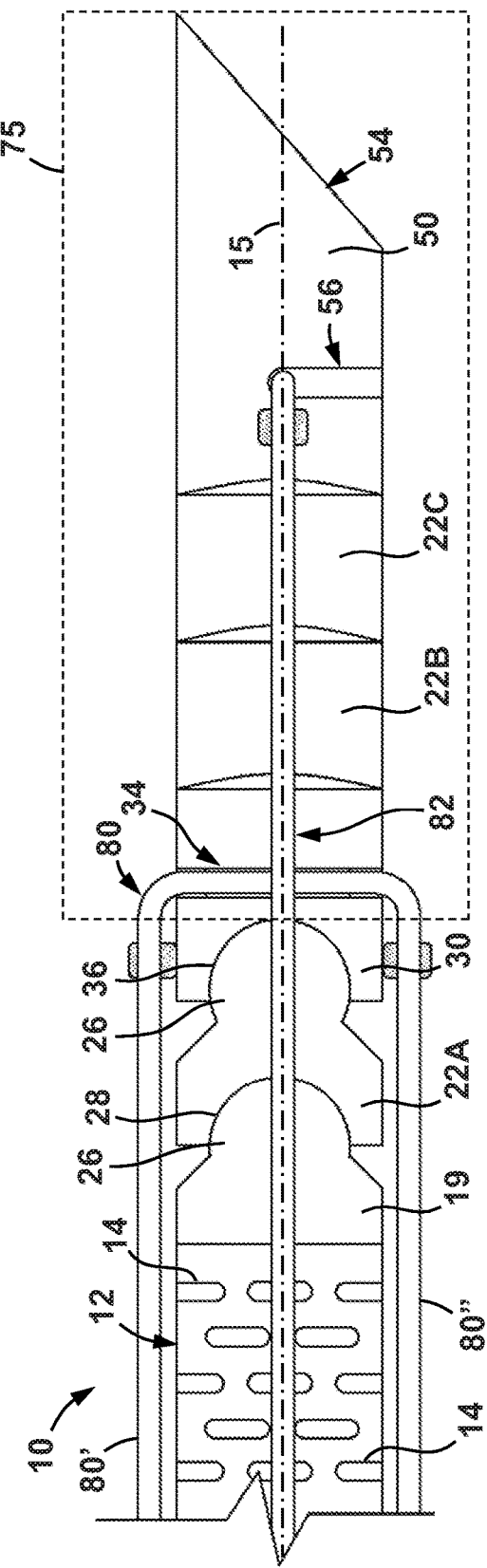

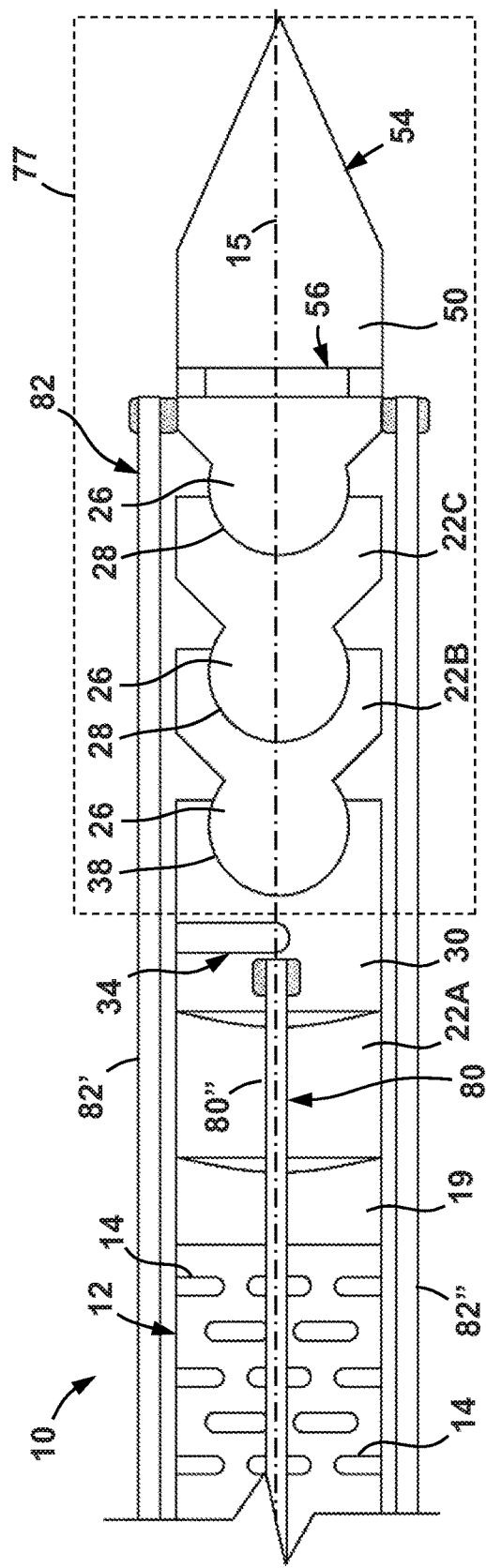
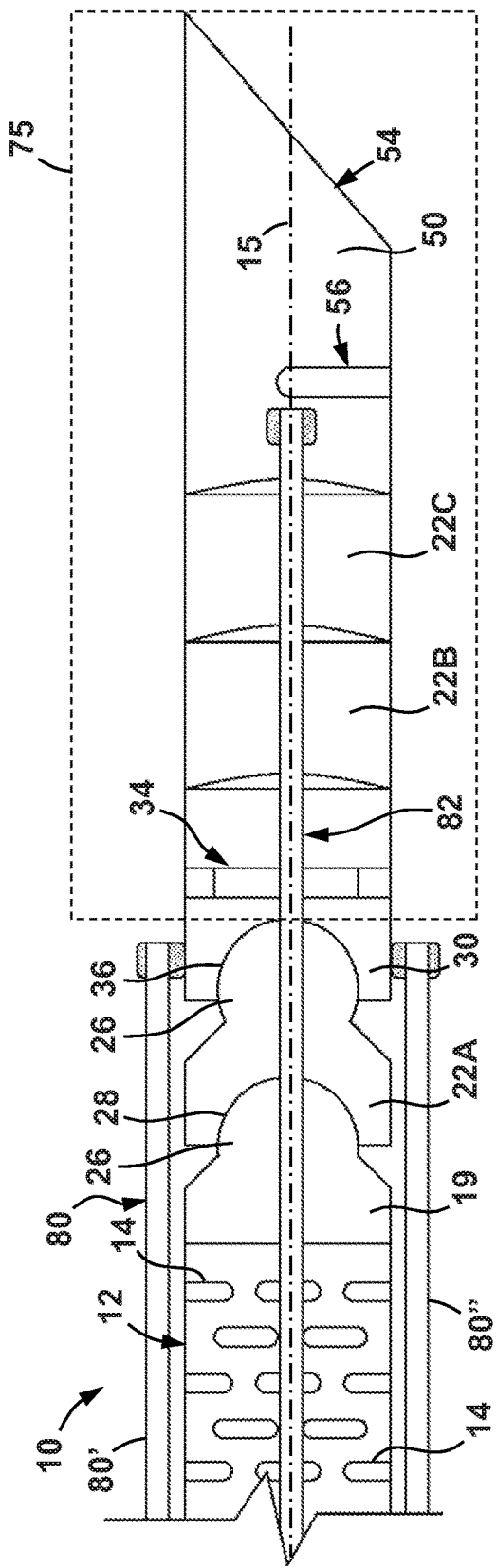

SURGICAL CANNULAS AND RELATED METHODS

CROSS-REFERENCE TO RELATED APPLICATIONS

This application claims benefit of U.S. provisional patent application Ser. No. 62/674,281 filed May 21, 2018, and entitled "Laser-Patterned Micro-Cannulae with Sensorized Tendons as Universal Tip-Steerable Micro-Robotic Components," which is hereby incorporated herein by reference in its entirety.

STATEMENT REGARDING FEDERALLY SPONSORED RESEARCH OR DEVELOPMENT

Not applicable.

BACKGROUND

Surgical procedures may involve the insertion of a tubular member (which may generically be referred to herein as a "cannula") into a body of a patient. The tubular member may be used to guide or deliver other surgical tools or implements, fluids, medications, sensors, etc. to a desired location within the patient's body. Some cannulas may be "steerable" in order to allow the physician to maneuver the cannula along or within a desired pathway in the body, and to place the distal end of the cannula at a desired location. In addition, some robotic surgical devices may make use of such steerable cannulas when performing surgical procedures.

BRIEF SUMMARY

Some embodiments disclosed herein are directed to a method of manufacturing a surgical cannula. In an embodiment, the method includes (a) providing an elongate tubular member, and (b) cutting one or more lines in the tubular member to form a tubular body and a hinge. The tubular body is pivotably coupled to the hinge. One of the tubular body and the hinge comprise a pin, and the other of the tubular body and the hinge comprise a socket, and (b) includes forming the pin within the socket by cutting the one or more lines.

Other embodiments disclosed herein are directed to a surgical cannula. In an embodiment, the surgical cannula includes a tubular body, a distal tip coupled to the tubular body, and a tendon coupled to the distal tip, wherein application of a tension to the tendon is configured to displace the distal tip. In addition the surgical cannula includes a fiber brag grating (FBG) reflector mounted to the tendon such that a tension in the tendon causes a strain on the FBG reflector. Further, the surgical cannula includes a controller coupled to the FBG reflector. The controller is configured to receive reflected light from the FBG filter and to determine the tension in the tendon based on the received reflected light.

In another embodiment, the surgical cannula includes a central axis, a tubular body, and a distal tip coupled to the tubular body such that the distal tip is configured to deflect relative to the tubular body. In addition, the surgical cannula includes a plurality of apertures extending through the tubular body. Each of the apertures includes a first end and a second end circumferentially spaced from the first end, a first curved surface at the first end, and a second curved surface at the second end. In addition, each of the apertures includes a first pair of straight edges extending from the first curved surface, and a second pair of straight edges extending from the second curved surface. A first edge of the first pair of straight edges intersects a first edge of the second pair of edges at a first point. A second edge of the first pair of straight edges intersects a second edge of the second pair of edges at a second point. The first pair of edges converge toward one another when moving from the first curved surface to the first and second points, and the second pair of edges converge toward one another when moving from the second curved surface toward the first and second points.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which:

FIGS. 7 and 8 are side views of a segment of the hinge of the surgical cannula of FIG. 1;

FIGS. 11 and 12 are side views of the surgical cannula of FIG. 1;

FIGS. 14 and 15 are side views of another surgical cannula according to some embodiments;

DETAILED DESCRIPTION

Figure 1:
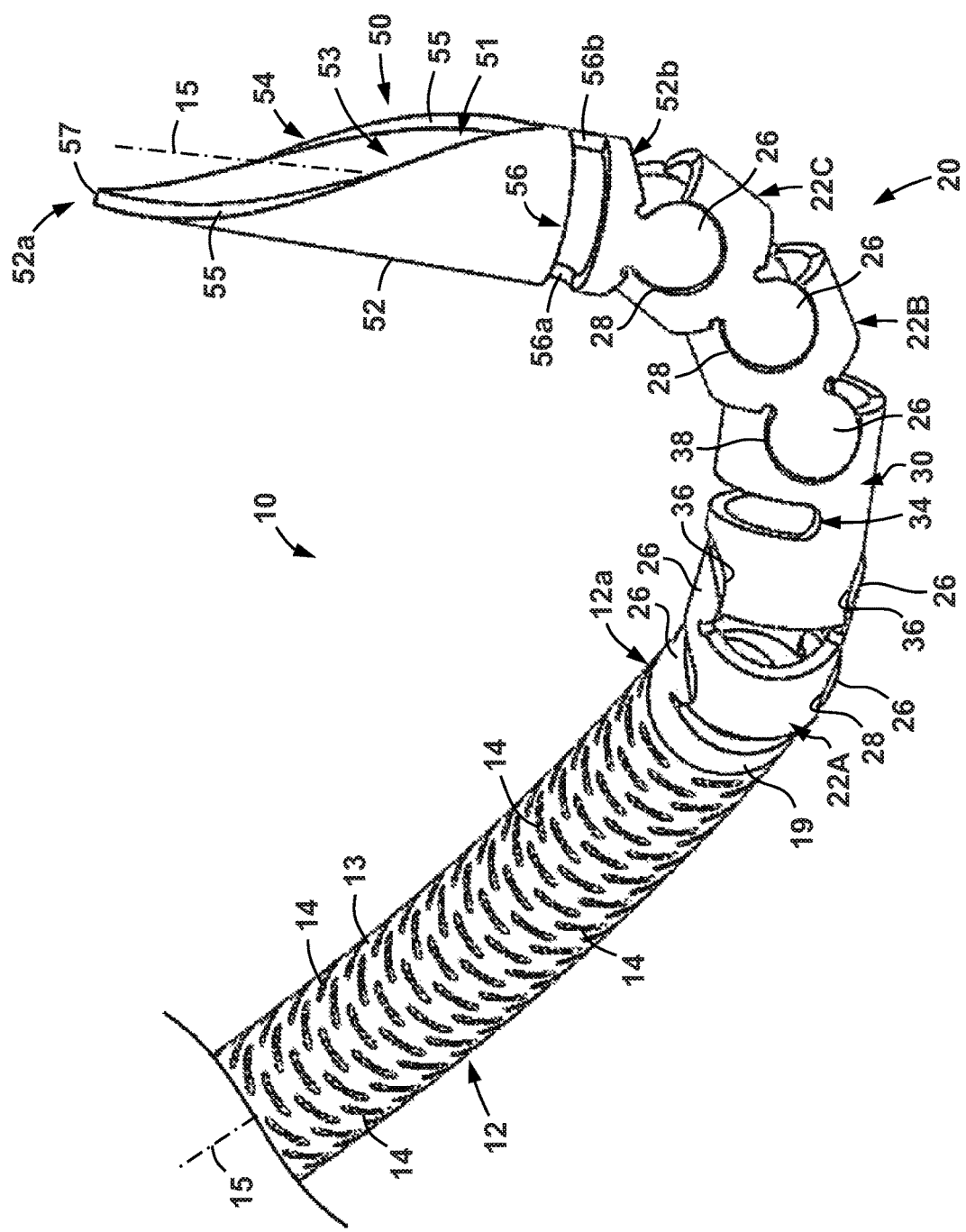
FIG. 1 is a perspective view of a surgical cannula according to some embodiments.

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. Further, when used herein (including in the claims), the words "about," "generally," "substantially," "approximately," and the like mean within a range of plus or minus 10%.

As previously described above, cannulas, such as steerable cannulas, may be used during a surgical procedure to introduce medication, tools, or other equipment into a body of a patient. During insertion of the cannula, it may be steered from the proximal end (e.g., by a physician and/or a surgical robot) to advance the tip of the cannula along a desired path within the patient's body. Such steering may be accomplished by selectively deforming or bending the cannula in a plurality of directions as the cannula is advanced into the body. In addition, the steering of the cannula is further facilitated by twisting or turning the cannula about its central axis, in concert with the selective deformation described above.

Given the relatively small size of steerable, surgical cannulas, it can be difficult (and therefore expensive) to manufacture the interlocking components that allow some or all of the above described deformations. Specifically, formation and subsequent assembly of the relatively small interlocking components or parts is particularly labor intensive and can lead to damage or weakening of the individual components. Also, some of the above described selective deformations of a surgical cannula may be accomplished by applying tension to one or more tendons extending axially along the cannula's. However, as the length of the cannula increases (e.g., to reach areas or locations within the body that are distally disposed from the access point along the patient's skin), the force or tension applied to the tendon for providing the desired deformation of the cannula tip may also increase. Thus, in some circumstances, the maximum allowable force or tension that may be borne by the tendon or even the cannula itself may be exceeded. Further, during a surgical procedure, it can be difficult to estimate or otherwise ascertain the reaction forces transferred to the cannula from the surrounding tissue.

Accordingly, some embodiments disclosed herein include surgical cannulas that include a plurality of patterned holes or apertures therein to enhance axial bending or deformation, while maintaining sufficient torsional rigidity to facilitate steering of the cannula during operations. In addition, some embodiments of the cannulas disclosed herein also include a deformable hinge comprising a plurality of axially adjacent pivotably coupled components that may be formed in situ from a solid tubular member so as to avoid the tedious and potentially damaging assembly process described above. Further, some embodiments disclosed herein include force sensing tendons for deflecting or deforming the tip of the cannula during operations that may allow the physician or operator (or robotic surgical device) to actively and accurately monitor the force or tension loads placed on the tendons and the cannula during operations.

Referring now to FIG. 1, an embodiment of a surgical cannula 10 according to some embodiments is shown. Cannula 10 includes a central or longitudinal axis 15 (that may bend and flex along with cannula 10 as shown in FIG. 1), a tubular body 12, a hinge 20, and a distal tip 50. The distal tip 50 is disposed at a distal end of the cannula 10. In addition, the hinge 20 is axially disposed between distal tip 50 and tubular body 12.

Figure 2:
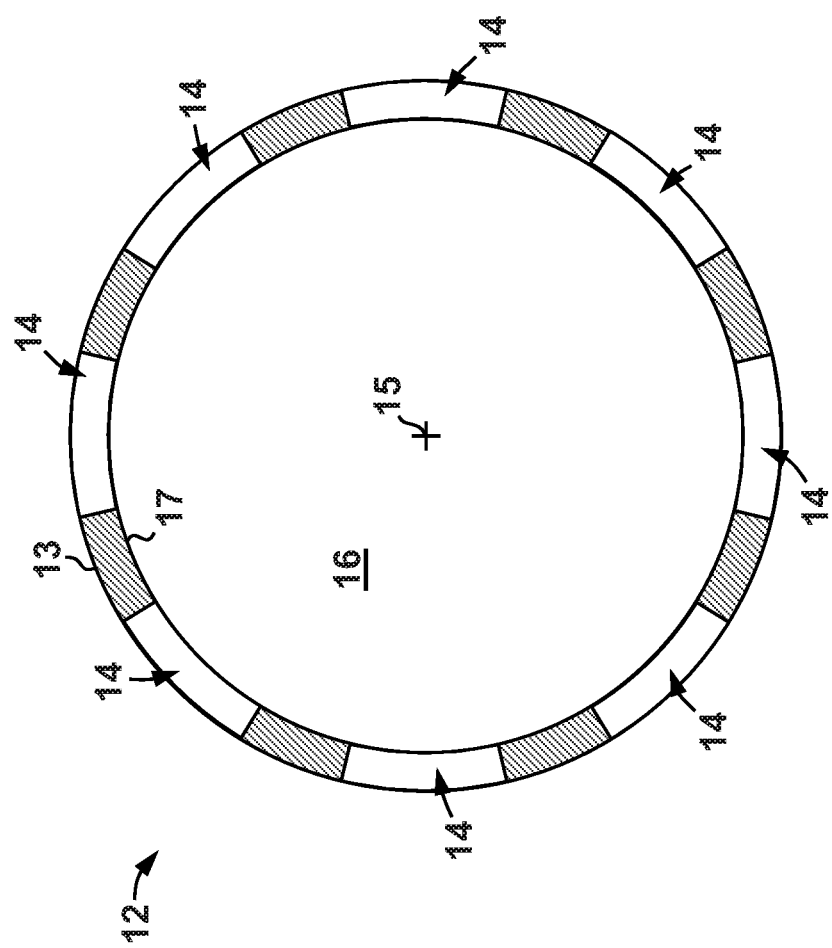
FIG. 2 is a cross-sectional view of the tubular body of the surgical cannula of FIG. 1.

Referring now to FIGS. 1 and 2, tubular body 12 is an elongate, tubular member that includes a proximal end (not shown) and a distal end 12a opposite proximal end along axis 15. In some embodiment, tubular body 12 includes a cylindrical cross-section and includes a radially outermost surface 13 and a radially inner most surface 17. In some embodiments, the radially outermost surface 13 and the radially inner most surface 17 are cylindrical surfaces; however, surfaces 13, 17 may include other shapes (e.g., oval, polygonal, triangular, rectangular, etc.) in other embodiments. The radially inner most surface 17 defines a central, axially extending throughbore or lumen 16 that extends from proximal end (not shown) to distal end 12a.

Figure 3:
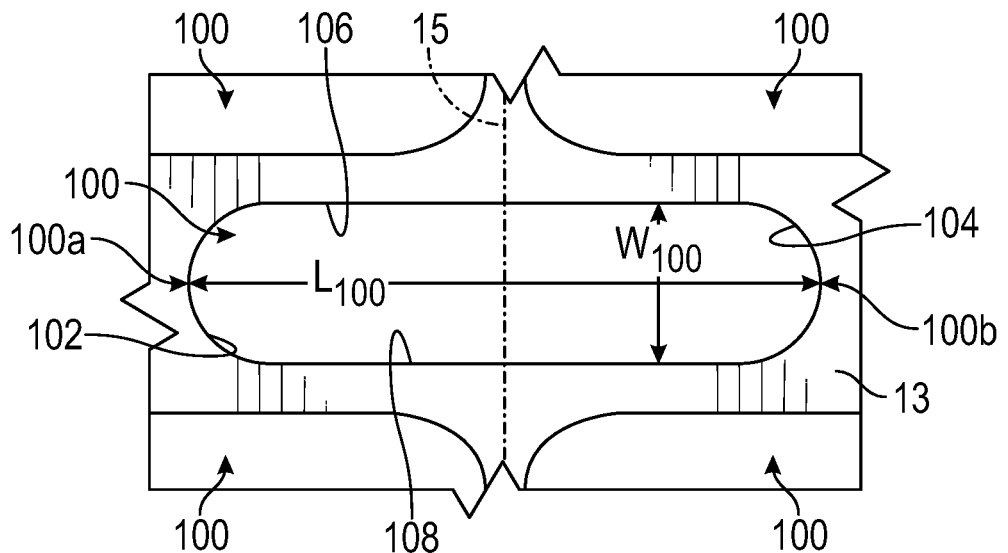
FIG. 3 is a side view of an aperture that may be utilized along the tubular body of the surgical cannula of FIG. 1 according to some embodiments.
Figure 4:
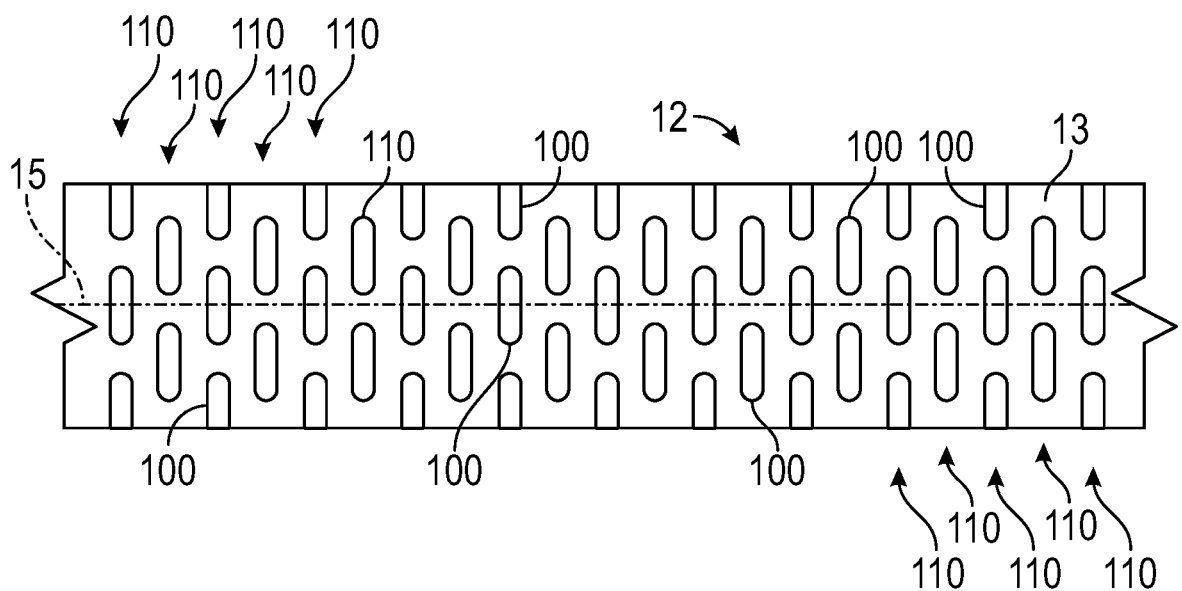
FIG. 4 is a side view of the tubular body of the surgical cannula of FIG. 1 according to some embodiments.
Figure 5:
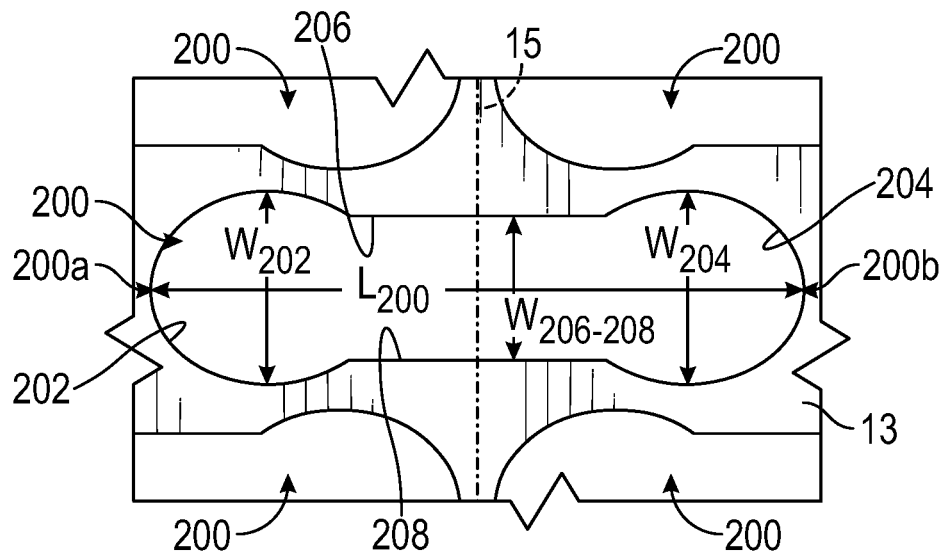
FIG. 5 is a side view of another aperture that may be utilized along the tubular body of the surgical cannula of FIG. 1 according to some embodiments.

In addition, tubular body 12 includes a plurality of patterned holes or apertures 14 extending generally radially through the radially outermost surface 13 and the radially innermost surface 17. Thus, apertures 14 extend into central throughbore 16. As best shown in FIG. 1, the apertures 13 are arranged in a repeating pattern that extends both circumferentially and axially with respect to axis 15. In some embodiments, each of the apertures 13 have the same shape. For instance, reference is now generally made to FIGS. 3-5 which show embodiments of apertures 14 that may be disposed along tubular body 12 in some embodiments. Each of the embodiments of apertures 13 shown in FIGS. 3-5 are described in turn below. It should be noted that axis 15 is generally shown in FIGS. 3-5 so as to better show the relative orientation of the apertures depicted therein.

In some embodiments, some or all of the apertures extending through tubular body 12 (e.g., apertures 14 in FIG. 1) may be shaped or formed as an elongated, rounded slot. For instance, reference is now made to FIG. 3 which shows an aperture 100 that may be formed in tubular body 12 (e.g., see FIG. 1). Aperture 100 includes a first end 100a and second end 100b circumferentially separated from first end 100a about axis 15. A first curved surface 102 is formed at first end 100a, and a second curved surface 104 is formed at second end 100b. In some embodiments (such as the embodiment of FIG. 3), curved surfaces 102, 104 are generally circular in shape; however, other curvatures are contemplated (e.g., oval, elliptical, parabolic, hyperbolic, etc.). In addition, aperture 100 includes a pair of straight sides or edges 106, 108 that extend circumferentially between curves surfaces 102, 104. Each of the sides 106, 108 are axially separated from one another along axis 15 so as to define the opening of aperture 100 through surfaces 13, 17 of tubular body 12 (see e.g., FIG. 1). In this embodiment, sides 106, 108 each extend tangentially from the curved surfaces 102, 104 at ends 100a, 100b, respectively. Aperture 100 may include a maximum length $L_{100}$ extending circumferentially between ends 100a, 100b, and a maximum width $W_{100}$ that extends axially between sides 106, 108. Aperture 100 is generally elongate such that length $L_{100}$ is greater than the width $W_{100}$. Generally speaking, in some embodiments the length $L_{100}$ and width $W_{100}$ may range from a few micrometers to a few millimeters, depending on the size (e.g., diameter, thickness, length, etc.) of the tubular body 12. In addition, in some embodiments, the apertures 100 may have an aspect ratio $L_{100}/W_{100}$ that that is greater than 1.

Referring now to FIG. 4, the apertures 100 are arranged along tubular body 12 in a plurality of axially spaced rows 110. Each row 110 includes a plurality of apertures 100 uniformly-circumferentially spaced form one another about axis 15. In addition, the apertures 100 of each row 110 are circumferentially misaligned or shifted from the apertures 100 in each immediately axially adjacent row 110, so that apertures 100 are generally uniformly spaced about tubular body 12.

Without being limited to this or any other theory, the arrangement, shape, and alignment of apertures 100 along body 12 generally increases the flexibility of tubular body 102 such that tubular body 12 may be generally flexed, bent, or otherwise deformed along axis 15. However, because apertures 100 are generally elongate and extend circumferentially about axis 15, tubular body 12 may still be substantially rigid in response to torsion about axis 15 (i.e., tubular body 12 generally resists torsional deformation while generally allowing bending or deflections of axis 15). As a result, apertures impart a so-called auxetic behavior (or a negative Poisson's Ratio) to tubular body 12.

Referring now to FIG. 5, an aperture 200 is shown that may be formed on tubular body 12 (see e.g., FIG. 1) in some embodiments. In this embodiment, apertures 200 may have a so-called "dog bone" shape or profile. Aperture 200 includes a first end 200a and second end 200b circumferentially separated from first end 200a about axis 15. A first curved surface 202 is formed at first end 200a, and a second curved surface 204 is formed at second end 200b. In some embodiments (such as the embodiment of FIG. 3), curved surfaces 102, 104 are generally elliptical in shape; however, other curvatures are contemplated (e.g., circular, parabolic, hyperbolic, etc.). In addition, aperture 200 includes a pair of axially spaced straight sides or edges 206, 308 that extend circumferentially between curves surfaces 202, 204. Aperture 200 may include a maximum length $L_{200}$ extending circumferentially between ends 200a, 200b. In addition, aperture 200 has a first pair of maximum widths $W_{202}$, $W_{204}$ extending axially across curved surfaces 202, 204, respectively, that are generally greater than a maximum width $W_{206-208}$ extending axially between sides 206, 208. Thus, the curved surfaces 202, 204 extend axially outside of sides 206, 208 such that aperture 200 has a so-called "dog bone" shape as previously described. As with aperture 100, aperture 200 is generally elongate such that the length $L_{200}$ is greater than each of the widths $W_{202}$, $W_{204}$, $W_{206-208}$. Generally speaking, in some embodiments the length $L_{200}$ and widths $W_{202}$, $W_{204}$, $W_{206-208}$ may range from a few micrometers to a few millimeters, depending on the size (e.g., diameter, thickness, length, etc.) of the tubular body 12. In addition, in some embodiments, the apertures 200 may have an aspect ratio $L_{200}/W_{202}$ or of $L_{200}/W_{204}$ that is greater than 1.

Referring now to FIGS. 4 and 5, in the same manner as described above for apertures 100, the apertures 200 are arranged along tubular body 12 in a plurality of axially spaced rows (e.g., rows 110 in FIG. 4). In addition, the apertures 200 have the same circumferential and axial spacing within the rows (e.g., rows 110) that is previously described above with respect to the apertures 100 and generally shown in FIG. 4. Thus, the description of the relative arrangement of apertures 200 within the axially spaced rows is not repeated herein in the interest of brevity.

Without being limited to this or any other theory, the arrangement, shape, and alignment of apertures 200 impart an auxetic behavior to tubular body 12 for substantially the same reasons discussed above with respect to aperture 100. As a result, when tubular body 102 includes the dog-bone style apertures 200, the tubular body 12 is configured to generally resist torsional deformation while also being generally configured to bend and flex along axis 15.

Figure 6:
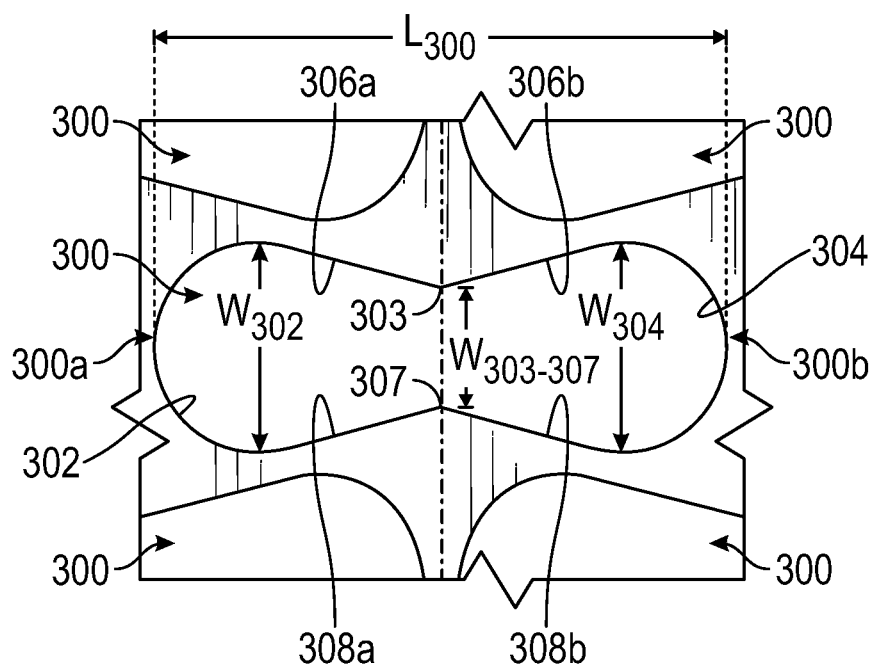
FIG. 6 is a side view of another aperture that may be utilized along the tubular body of the surgical cannula of FIG. 1 according to some embodiments.

Referring now to FIG. 6, an aperture 300 is shown that may be formed on tubular body 12 (see e.g., FIG. 1) in some embodiments. In this embodiment, apertures 300 may have a so-called "rounded re-entrant honeycomb" shape or profile. Aperture 300 includes a first end 300a and second end 300b circumferentially separated from first end 300a about axis 15. A first curved surface 302 is formed at first end 300a, and a second curved surface 304 is formed at second end 300b. In some embodiments (such as the embodiment of FIG. 3), curved surfaces 302, 304 are generally circular in shape; however, other curvatures are contemplated (e.g., oval, elliptical, parabolic, hyperbolic, etc.). In addition, aperture 300 includes a first pair of straight edges 306a, 308a that extend tangentially from curved surface 302 and a second pair of straight edges 306b, 308b that extend tangentially from curved surface 304. The first pair of straight edges 306a, 306b converge toward one another along axis 15 as they extend circumferentially from first curved surface 302, and the second pair of straight edges 306b, 308b converge toward one another along axis 15 as they extend circumferentially from second curved surface 304. The edges 306a, 306b meet at a point or corner 303, and the edges 308a, 308b meet at a point or corner 307. The corners 303, 307 are generally circumferentially equidistant from ends 300a, 300b, and are axially spaced from one another along axis 15.

Aperture 300 may include a maximum length $L_{300}$ extending circumferentially between ends 300a, 300b. In addition, aperture 200 has a first pair of maximum widths $W_{302}$, $W_{304}$ extending axially across curved surfaces 302, 304, respectively, that are generally greater than a maximum width $W_{306-308}$ extending axially between corners 303, 307. Thus, the curved surfaces 202, 204 extend axially outside of corners 303, 307, sides 306a, 308a extend linearly from points 303, 307 to first curved surface, and sides 306b, 308b extend linearly from points 303, 307 to second curved surface 304. As a result, aperture 300 has a so-called "rounded re-entrant honeycomb" shape as previously described. As with aperture 100, aperture 300 is generally elongate such that the length $L_{300}$ is greater than each of the widths $W_{302}$, $W_{304}$, $W_{303-307}$. Generally speaking, in some embodiments the length $L_{300}$ and widths $W_{302}$, $W_{304}$, $W_{303\text{-}307}$ may range from a few micrometers to a few millimeters, depending on the size (e.g., diameter, thickness, length, etc.) of the tubular body 12. In addition, in some embodiments, the apertures 300 may have an aspect ratio $L_{300}/W_{302}$ or of $L_{300}/W_{304}$ that ranges is greater than 1.

Referring now to FIGS. 4 and 6, in the same manner as described above for apertures 100, the apertures 300 are arranged along tubular body 12 in a plurality of axially spaced rows (e.g., rows 110 in FIG. 4). In addition, the apertures 300 have the same circumferential and axial spacing within the rows (e.g., rows 110) that is previously described above with respect to the apertures 100 and generally shown in FIG. 4. Thus, the description of the relative arrangement of apertures 300 within the axially spaced rows is not repeated herein in the interest of brevity.

Without being limited to this or any other theory, the arrangement, shape, and alignment of apertures 300 impart an auxetic behavior to tubular body 12 for substantially the same reasons discussed above with respect to aperture 100. As a result, when tubular body 102 includes the rounded re-entrant honeycomb style apertures 300, the tubular body 12 is configured to generally resist torsional deformation while also being generally configured to bend and flex along axis 15.

Referring again to FIG. 1, the apertures 14 (or apertures 100, 200, 300, etc.) may be formed, in some embodiments, via a laser machining process. In particular, during operations, a laser is directed onto radially outermost surface 13 of tubular member 12 to generate a high heat flux that melts and/or vaporizes the material to thereby form the desired aperture shape (e.g., apertures 100, 200, 300, etc.). Any suitable laser may be used for this process, such as, for example a $CO_2$ laser or a neodymium yttrium aluminum garnet laser. In some embodiments, apertures 14 (e.g., or apertures 100, 200, 300, etc.) may be formed by directing the laser along a radius of axis 15 (e.g., such that the laser points toward axis 15 during cutting operations); however, in other embodiments, the laser may be directed along a non-radial path (i.e., one that does not pass through axis 15) during a laser cutting operation for tubular member 12.

Tubular body 12 may comprise any suitable material for a surgical device. In some embodiment, tubular body 12 comprises a metal, such as, for example nickel-titanium (e.g., Nitinol). In some embodiments, tubular body 12, hinge 20, and distal tip 50 all comprise the same material.

Referring still to FIG. 1, hinge 20 includes a plurality of segments that are pivotably coupled to one another along axis 15 so that allow hinge 20 to flex or bend in a plurality of different directions or planes. In particular, in some embodiments hinge 20 includes a plurality of first segments 22 and a second segment 30 all pivotably coupled to one another. It should be appreciated that in other embodiments, hinge 20 includes different numbers and arrangements of segments 22, 30 than that described below for the embodiment of FIG. 1. For instance, in some embodiments, hinge 20 may include only first segments 22 (either one or a plurality thereof), only second segments 30 (either one or a plurality thereof), or a combination of first segments 22 and second segments 30 (again, either one or a plurality of either or both segments 22, 30).

Referring now to FIGS. 7 and 8, each first segment includes a body 24 including a first end 24a, a second end 24b opposite first end 24a, and a throughbore 21 extending axially (along axis 15) between ends 24a, 24b. In some embodiments, body 24 is cylindrical in shape; however, other shapes are possible and contemplated for other embodiments (e.g., square, triangular, rectangular, polygonal, etc.).

A pair of pins 26 extend axially from second end 24b of body 24 that radially oppose one another across axis 15 (i.e., pins 26 are disposed approximately 180° apart from one another about axis 15). As best shown in FIG. 7 (which only depicts one of the pins 26), pins 26 are generally circular in shape; however, other curved shapes for pins 26 may be used in other embodiments. In addition, second end 24b of body may include a ramped or sloped surface 27 that extends from pins 26 at a non-zero angle θ relative to a radius of axis 15. Without being limited to this or any other theory and as will be described in more detail below, during operations the clearance provided by ramped surfaces 27 may allow axially adjacent and pivotably coupled segments 22, 30 to pivot within a desired range of motion.

Referring still to FIGS. 7 and 8, a pair of apertures or sockets 28 extends into body 24 from first end 24a. Sockets 28 are radially opposite one another about axis 15, and in this embodiment, sockets 28 are substantially circumferentially aligned with pins 26 about axis 15. Thus, in some embodiments, each socket 28 is disposed on the same circumferential side of body 24 as a corresponding one of the pins 26. As with pins 26, in some embodiments, sockets 28 are circular in shape; however, other curved shapes for pins 26 may be used in other embodiments. In some embodiments, sockets 28 are shaped to correspond with the shape of pins 26, such that the pins 26 of one segment 22 may be received within the sockets 28 of an axially adjacent segment 22 within hinge 20, which will be described in more detail below (see e.g., FIG. 1).

Figure 10:
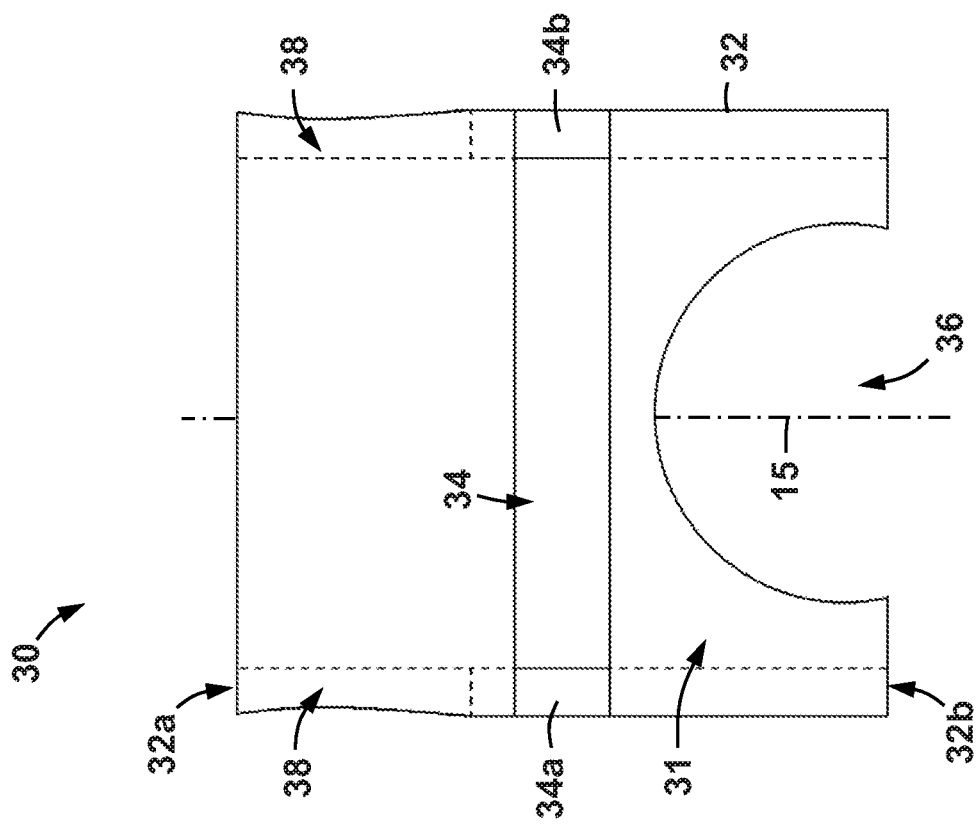
FIGS. 9 and 10 are a side views of another segment of the hinge of the surgical cannula of FIG. 1.
Figure 9:
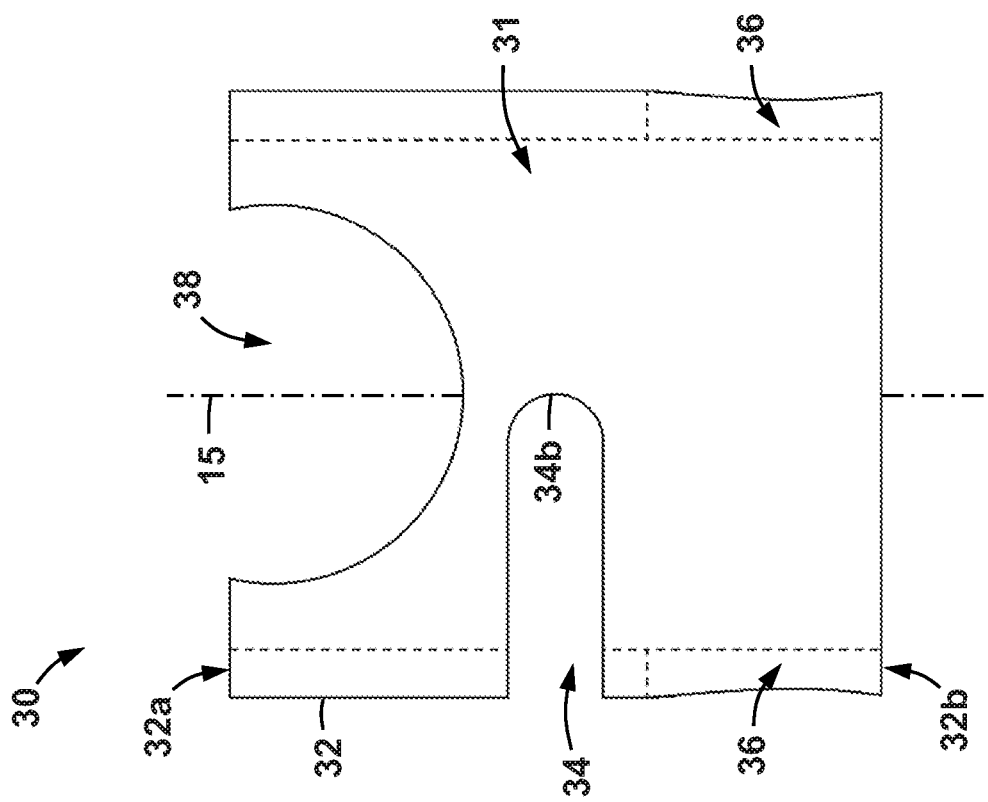

Referring now to FIGS. 9 and 10, second segment 30 includes a body 32 including a first end 32a, a second end 32b opposite first end 32a, and a throughbore 31 extending axially (along axis 15) between ends 32a, 32b. In some embodiments, body 32 is cylindrical in shape; however, other shapes are possible and contemplated for other embodiments (e.g., square, triangular, rectangular, polygonal, etc.).

A first pair of sockets 36 extend axially into body 32 from second end 32b that radially oppose one another across axis 15 (i.e., sockets 36 are disposed approximately 180° apart from one another about axis 15). As best shown in FIG. 10 (which only depicts one of the sockets 36), sockets 36 are generally circular in shape; however, other curved shapes for sockets 36 may be used in other embodiments.

A second pair of sockets 38 extend axially into body 32 from first end 32a that radially oppose one another across axis 15 (i.e., sockets 38 are disposed approximately 180° apart from one another about axis 15). As best shown in FIG. 9 (which only depicts one of the sockets 38), sockets 38 are generally circular in shape; however, other curved shaped for sockets 36 may be used in other embodiments. In addition, the second sockets 38 are circumferentially shifted from the positions of the first sockets 36. In particular, in some embodiments, the second sockets 38 are shifted approximately 90° about axis form first sockets 36.

Referring still to FIGS. 9 and 10, second segment 30 also includes a slot 34 extending radially inward toward axis 15. Slot 34 includes a first end 34a and a second end 34b circumferentially spaced from first end 34a about axis 15. In particular, in some embodiments ends 34a, 34b are radially opposite one another about axis 15 such that ends 34a, 34b are disposed approximately 180° from one another about axis 15. However, other spacing values for ends 34a, 34b both above and below 180° about axis 15 are contemplated.

Referring again to FIG. 1, a connector 19 is mounted to distal end 12a of tubular body 12 that includes a pair of pins 26 that are substantially the same as pins 26 on first segments 22 (previously described). One of the first segments 22 (which is designated in FIG. 1 and the text below as segment 22A) is pivotably coupled to connector 12 such that pins 26 on connector 19 are pivotably received within sockets 28 of the first segment 22A. Next, second segment 30 is pivotably coupled to segment 22A such that the pins of segment 22A are pivotably received within the first sockets 36 of second segment 30. Pins 26 of connector 19 and segment 22A are circumferentially aligned along axis 15 such that segments 22A, 30 may pivot within a first longitudinal plane that includes axis 15, relative to tubular body 12 (see e.g., the plane 75 extending along and including axis 15 that extends into the page in the view of FIG. 12). In addition, slot 34 on second segment 30 is positioned such that it is circumferentially centered with the pins 26 of segment 22A and connector 19.

Next, a second one of the first segments 22 (which is designated in FIG. 1 and the text below as segment 22B) is pivotably coupled to second segment 30 such that pins 26 of segment 22B are pivotably received within second sockets 38 of segment 30. In addition, in the embodiment FIG. 1, another of the first segments 22 (which is designated in FIG. 1 and the text below as segment 22C) is pivotably coupled to the segment 22B such that the pins 26 of segment 22C are pivotably received within the sockets 28 of segment 22B. Each the pins 26 of segment 22 are circumferentially aligned with the pins 36 of segment 22C about axis 15, such that segments 22B, 22C may pivot within a second longitudinal plane that includes axis 15 relative to second segment 30 (see e.g., the plane 77 extending along and including the axis 15 that extends along the page in the view of FIG. 11). The second longitudinal plane (within which the segments 22B, 22C may pivot as described above) is shifted approximately 90° about axis 15 from the first longitudinal plane (within which the segments 22A and 30 may pivot as described above) (see e.g., planes 75, 77 in FIGS. 11 and 12) such that the first and second longitudinal planes are orthogonal to one another.

Referring still to FIG. 1, the segments (e.g., segments 22, 30) of hinge 20 may be formed via a laser cutting or machining operation similar to that previously described above for forming apertures 14 (e.g., or apertures 100, 200, 300, etc.). Thus, hinge 20 may be formed or manufactured by starting with a continuous hollow cylindrical member and then cutting, via a laser, the various channels and edges to form the sockets 28, 36, 38, pins 26, and slot 24 of segments 22, 30 as previously described above. Accordingly, the formation of segments 22, 30 and the assembly of segments 22, 30 to form hinge 20 may be performed in a single manufacturing step (e.g., laser machining). As a result, the pins 26 of segments 22, 30 may be formed within the corresponding sockets 28, 36, 38 as described above, such that insertion of pins 26 within sockets 28, 36, 38 is not necessary. In addition to being tedious, such insertion operations can cause damage (e.g., weakening, plastic deformation, etc.) to the relatively fragile pins 26 (and possible sockets 28, 36, 38), and thus by avoiding these insertion operations, the structural integrity of the hinge 20 may be ensured. During the single step laser machining operation, the laser may be directed radially toward axis 15 and/or may be directed along a non-radial path as previously described above (e.g., with respect to the laser machining of apertures 14, 100, 200, 300, etc.).

Referring still to FIG. 1, distal tip 50 includes a generally cylindrical body 52 including a first end 52a, a second end 52b opposite first end 52a, and a throughbore 51 extending axially between ends 51. A pair of pins 26, each being the same as previously described above for segments 22, extend axially from second end 52b. As with the pins 26 on segments 22, the pins 26 on distal tip 50 are radially opposite one another about axis 15 (i.e., pins 26 on distal tip 50 are disposed approximately 180° apart from one another about axis 15). In addition, a bevel 54 is formed on body 52 that extends to first end 52a. In this embodiment, bevel 54 is defined by a pair of helical surfaces 55 that meet or intersect at a sharp point or tip 57 at first end 52a. In other embodiments, helical surfaces 55 may be replaced with substantially planar or flat surfaces, or any suitably shaped surfaces. The helical surfaces 55 forming bevel 54 also form an opening 53 into throughbore 51 at first end 52a.

Further, body 52 of distal tip 50 also includes a slot 56 extending radially inward toward axis 15. Slot 56 may be axially spaced between bevel 54 and second end 52b of body 52. Slot 56 includes a first end 56a and a second end 56b circumferentially spaced from first end 56a about axis 15. In particular, in some embodiments ends 56a, 56b are radially opposite one another about axis 15 such that ends 56a, 56b are disposed approximately 180° from one another about axis 15. However, other spacing values for ends 56a, 56b both above and below 180° about axis 15 are contemplated herein.

As shown in FIG. 1, distal tip 50 is secured to a distal end of hinge 20 by inserting pins 26 on body 52 of distal tip 50 within the socket 28 of segment 22C. The pins 26 on distal tip 50 are circumferentially aligned with the pins 26 of segments 22B, 22C, and thus, distal tip 50 may pivot in the second longitudinal plane along with the segments 22B, 22C as previously described above. In addition, slot 56 on body 52 is positioned such that it is circumferentially centered with the pins 26 of body 52 and segments 22B, 22C, and therefore is shifted approximately 90° from slot 34 on second body 30.

Referring now to FIGS. 1, 2, and 7-10, once surgical cannula 10 is fully constructed, the throughbore 16 of tubular body is in communication and aligned with the throughbore 51 of distal tip 50 along axis 15 via the throughbores 21, 31 of segments 22, 30 within hinge 20. As a result, other surgical devices (e.g., guide wires, catheters, needles, etc.) may be inserted through surgical cannula 10 and out of opening 53 of distal tip 50 during operations. In addition, fluids or other substances (e.g., plasma, liquids, etc.) may be directed or channeled through cannula 10 (including tubular body 12, hinge, 20 and distal tip 50) and emitted from opening 53 during operations.

Referring now to FIGS. 1, 11, and 12, during operations a plurality of tendons secured to surgical cannula 10 may be selectively tensioned to steer distal tip 50 as cannula 10 is advanced within the body of a patient. Specifically, in this embodiment a first tendon 80 extends through slot 34 in second segment 30, and a second tendon 82 extends through slot 56 in distal tip 50. Tendons 80, 82 extend generally axially along tubular body 12 and are looped through the respective slots 34, 56. In addition, tendons 80, 82 are bonded to surgical cannula 10—with first tendon 80 being bonded to second segment 30, and second tendon 82 being bonded to distal tip 50. Tendons 80, 82 may be bonded to cannula 10 with any suitable material or method. For instance, in this embodiment, tendons 80, 82 are bonded to cannula with an adhesive 84 (e.g., an alkoxy-ethyl adhesive). Thus, each tendon 80, 82 has a pair of sides or legs that extend axially along tubular body 12. Specifically, first tendon 80 has a pair of legs 80', 80" that extend along radially opposite sides of tubular body 12 (see e.g., FIG. 12), and second tendon 82 has a pair of legs 82', 82" that extend along radially opposite sides of tubular body 12 (see e.g., FIG. 11). In this embodiment, each leg 80', 80", 82', 82" is individually bonded to cannula 10 with adhesive 84 (with legs 80', 80" each bonded to second segment 30 and legs 82', 82" bonded to distal tip 50). Because slots 34, 56 are shifted approximately 90° from one another about axis 15 as previously described above, legs 80', 80" of tendon 80 are also shifted approximately 90° from legs 82', 82" of tendon 82. During operations, legs 80', 80" are selectively tensioned (e.g., pulled) to move or deflect distal tip 50 within first longitudinal plane 75 shown in FIG. 12, and legs 82', 82" are selectively tensioned (e.g., pulled) to move or deflect distal tip 50 within second longitudinal plane 77 shown in FIG. 11.

Figure 13:
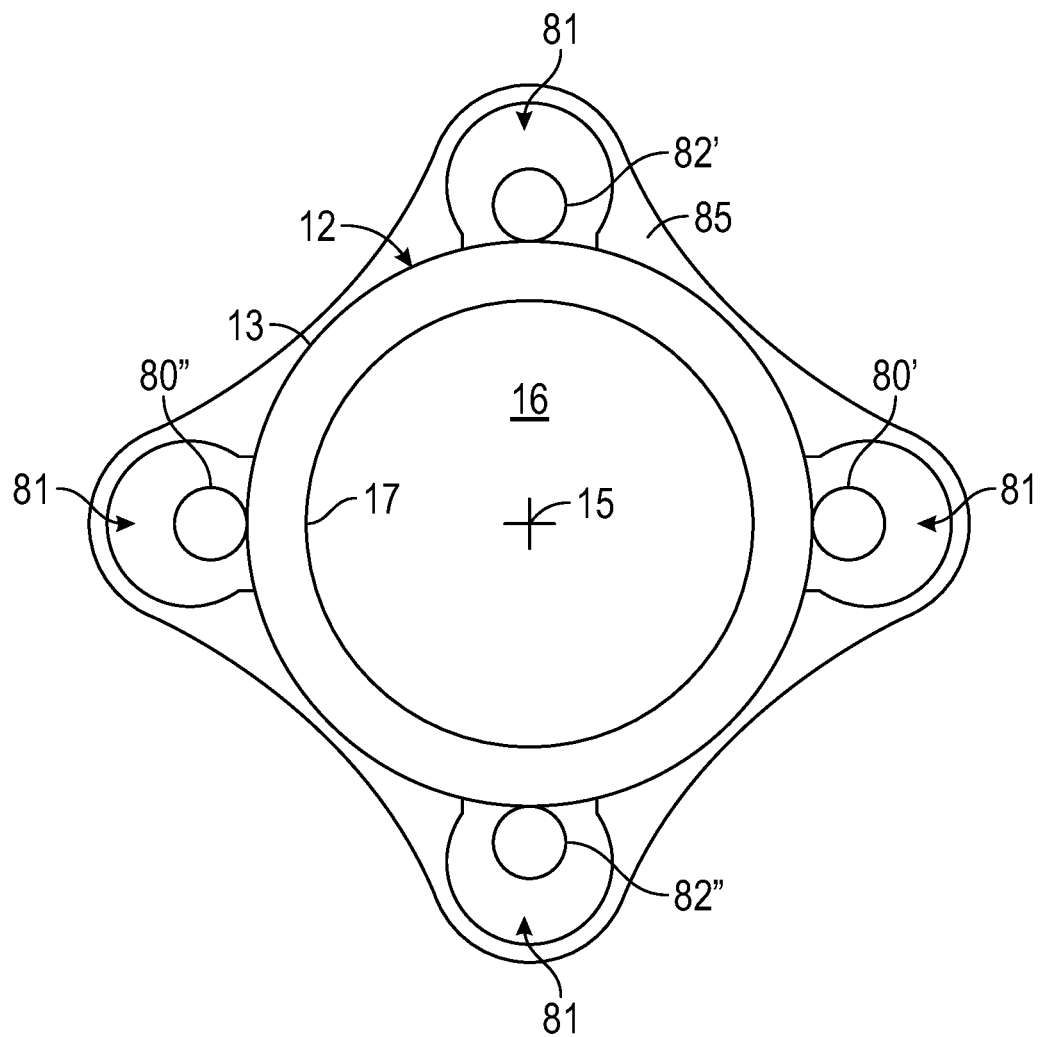
FIG. 13 is a cross-sectional view the tubular body of the surgical cannula of FIG. 1 according to some embodiments.

Referring briefly to FIG. 13, in some embodiments, a protective sheathing or covering 85 is disposed about tubular body 12 and possibly also some or all of hinge 20 that includes a plurality of axially extending throughbores or channels 81 that receive legs 80', 80", 82', 82" of tendons 80, 82 therethrough. Without being limited to this or any other theory, channels 81 are configured to protect legs 80', 80", 82', 82" during a surgical operation so as to ensure that tendons 80', 80", 82', 82" are not obstructed from axial movement and are separated from bodily fluids, tissue, etc.

In some embodiments, tendons 80, 82 are not looped through slots 34, 56. For example, reference is now made to FIGS. 14 and 15 which show legs 80', 80" of tendon 80 and legs 82', 82" of tendons 82 separated from one another and individually bonded to surgical cannula 10 with adhesive 84 in the same manner as described above. Accordingly, in the embodiment of FIGS. 14 and 15, legs 80', 80", 82', 82" each form individual tendons routed along surgical cannula 10, and operations with cannula 10 are the same as previously described with respect to the embodiment of FIGS. 11 and 12, and thus, they are not repeated again in the interest of brevity. Accordingly, selective tensioning of legs 80', 80" (ot tendons 80', 80") causes deflection of distal tip 50 within longitudinal plane 75, and selective tensioning of legs 82', 82" (or tendons 82', 82") causes deflection of distal tip 50 within longitudinal plane 77 in the same manner as described above.

Figure 16:
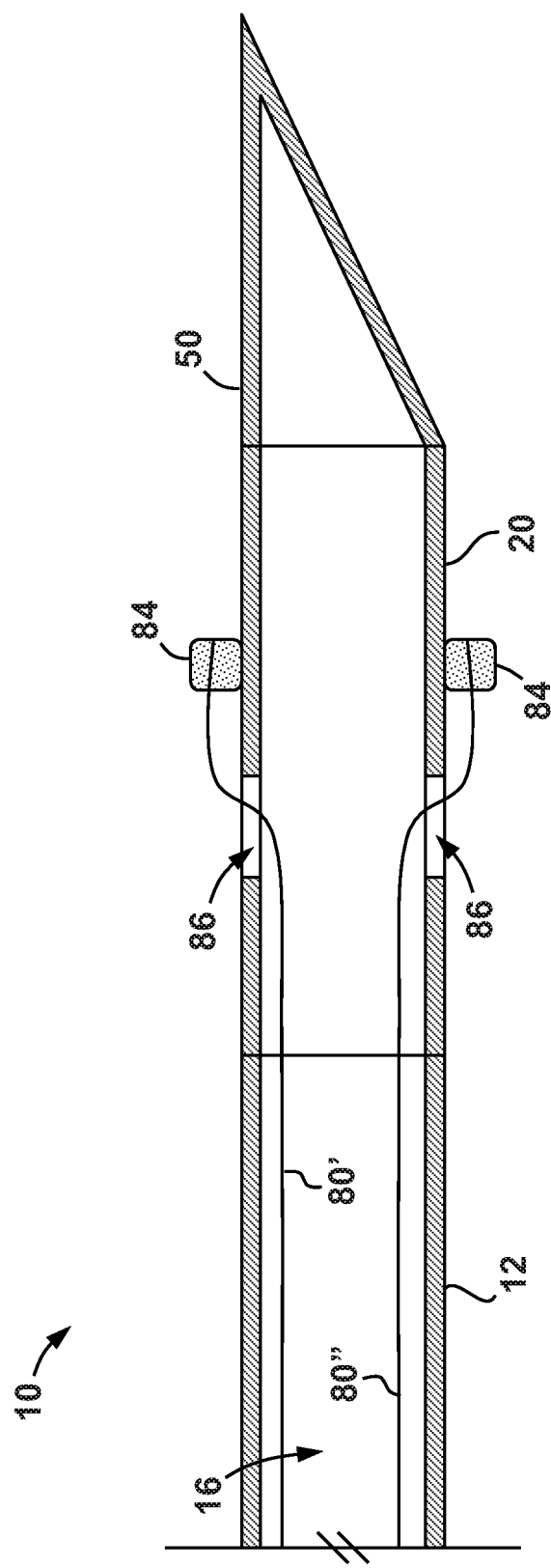
FIG. 16 is a schematic side cross-sectional view of another surgical cannula according to some embodiments.

In some embodiments, the tendons of surgical cannula 10 (e.g., tendons 80, 82) may be partially or totally routed within central throughbore 16 of tubular body 12. In particular, in the schematic example shown in FIG. 16, legs 80', 80" are bonded to an external surface of hinge 20 via adhesive 84 as previously described above, and then are routed through holes or ports 86 in hinge 20 (e.g., holes 86 may extend through any one or more of the segments 22, 30) such that legs 80', 80" may be routed through throughbore 16 of tubular body 12 back toward the proximal end of cannula 10. While note specifically shown, it should be appreciated that legs 82', 82" of tendons 82 (see e.g., FIGS. 11 and 12) may extend through similar holes 86 in distal tip 50 and/or hinge 20 and routed through throughbore 16 of tubular body 12 in the same manner as shown for legs 80', 80". Without being limited to this or any other theory, routing the tendons 80, 82 through throughbore 16 may reduce the outer width of cannula 10 and may also protect tendons 80, 82 from damage caused by abrasion between tendons 80, 82 and tissue or other objects during operations. In addition, in some embodiments, tendons (e.g., tendons 80, 82) may be routed both externally and internally through tubular body 12 (e.g., one or more of the legs 80', 80", 82', 82" may be routed through throughbore 16, and the remaining legs may be routed outside of throughbore 16).

Tendons 80, 82 may comprise any suitable material that may transfer sufficient tensile loads to deflect distal tip 50 and hinge 20 during operations. In some embodiment, tendons 80, 82 may comprise a metal, a polymer, a composite, etc. In some embodiments, tendons may comprise poly-paraphenylene terephthalamide (e.g., Kevlar®). In some embodiments, tendons 80, 82 may comprise fiber optic lines or cables.

Figure 17:
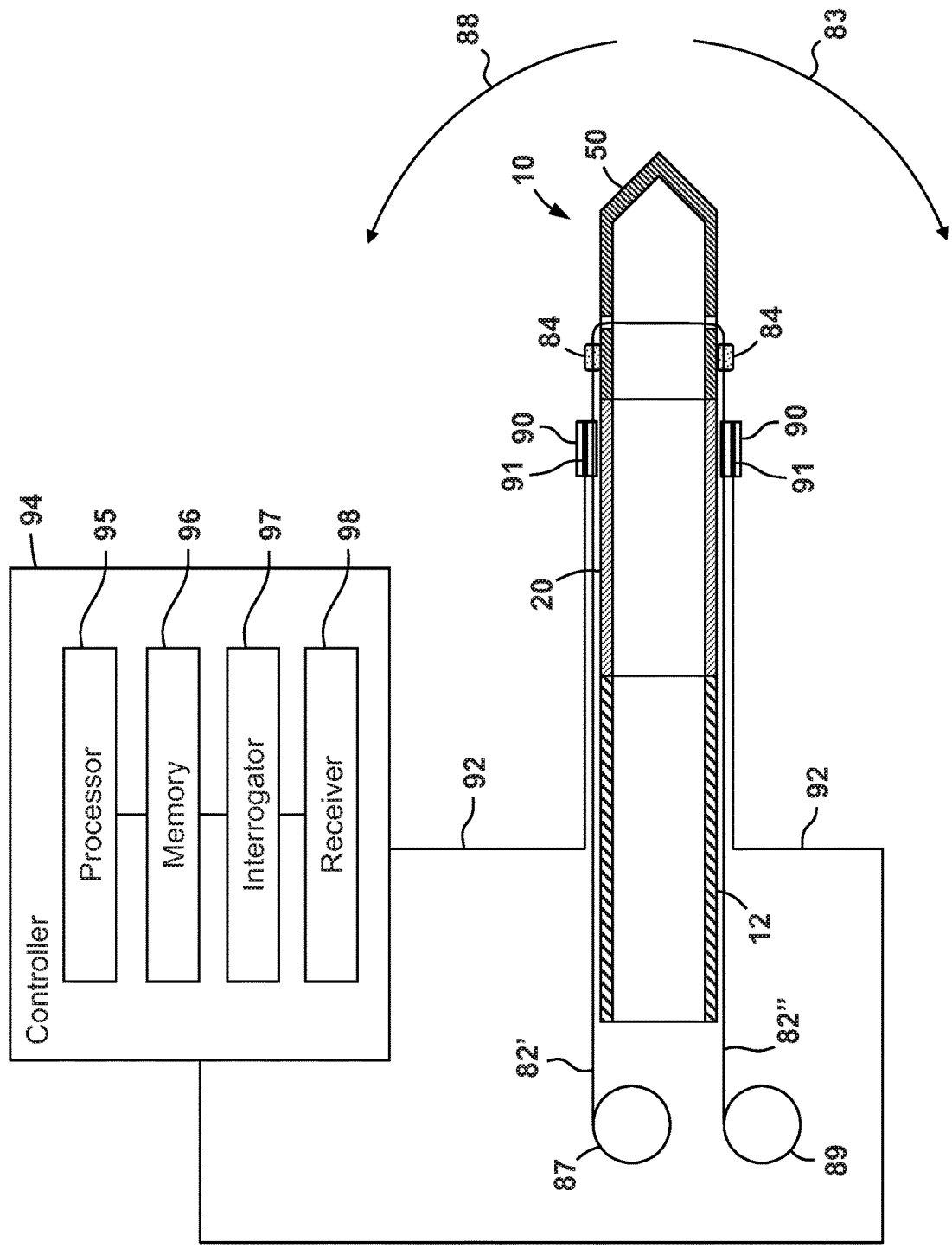
FIG. 17 is a schematic diagram of another surgical cannula according to some embodiments.

Referring now to FIG. 17, in some embodiments, the tendons 80, 82 may be "sensorized" so that the force or tension applied to tendons 80, 82 and also surgical cannula 10 may be actively measured during operations. For instance, a physician may wish to monitor the force loads transferred to cannula 10 during a surgical operation so as to ascertain the resistance being imparted to cannula 10 (e.g., at distal tip 50) by the surrounding tissue. In addition, in some circumstances, it may be beneficial to monitor the magnitude of tension applied to the tendons 80, 82 during steering operations so as to avoid over tensioning (and thereby damning) tendons 80, 82.

In the example of FIG. 17, only tendon 82 is shown so as to simplify the figure; however, it should be appreciated that the same technique described below may be applied to tendon 80 in substantially the same manner. In this embodiment, a fiber brag grating (FBG) reflector 91 is bonded to each leg 82', 82" with an adhesive 90, such as, for example, an alkoxy-ethyl adhesive, and a fiber optic line 92 is coupled to and routed from each reflector 91 to a controller 94. In some embodiments, FBG reflectors 91 may comprise a polarization maintaining FBG (PM-FBG), such as PM-FBG reflectors manufactured by Draw Tower Grating technology. In some embodiments, the PM-FBG reflectors 91 may include reinforcing wires or fibers (e.g., metal, polymer, etc.) such has fibers comprising titanium, poly-paraphenylene terephthalamide, etc. Each fiber optic line 92 may be routed alongside legs 82', 82", and thus fiber optic lines 92 may be extended within throughbore 16, within channels 81 in FIG. 13, etc. In some embodiments, fiber optic lines 92 may be bundled with legs 82', 82". Legs 82', 82" are each coupled to a corresponding actuator 87, 89, respectively, that are configured to apply a selective tension load during operations. While any suitable actuator may be used for actuators 87, 89, in this embodiment, actuators 87, 89 comprise rotary actuators.

Controller 94 may comprise any suitable device or assembly which is capable of receiving an electrical, optical, or mechanical signal and transmitting various signals to other devices. In particular, as shown in FIG. 17, in this example, controller 94 includes a processor 95 and a memory 96, and interrogator 97, and a receiver 98.

The processor 95 (e.g., microprocessor, central processing unit, or collection of such processor devices, etc.) executes machine-readable instructions (e.g., non-transitory machine readable medium) provided on memory 96, and upon executing the machine-readable instructions on memory 96 provides the controller 94 with all of the functionality described herein. The memory 96 may comprise volatile storage (e.g., random access memory), non-volatile storage (e.g., flash storage, read only memory, etc.), or combinations of both volatile and non-volatile storage. Data consumed or produced by the machine-readable instructions can also be stored on memory 96.

Interrogator 97 may comprise any suitable device to emitting light signals that are transmitted, via fiber optic lines 92, to filters 91. For instance, interrogator 97 may comprise a tunable laser interrogator, similar to those available from FAZ Technologies, located in Dublin Ireland. Receiver 98 may comprise any suitable device for receiving, characterizing, and analyzing light waves reflected back from filter 91 via fiber optic lines 92. Thus, receiver 98 may comprise appropriate light sensors for sensing the characteristics of the reflected light from reflectors 91 during operations. In some embodiments, receiver 98 is incorporated within interrogator 97. In addition, in some embodiments, controller 94 may be a standalone unit that includes processor 95, memory 96, interrogator 97, and receiver 98, or may comprise a plurality of different units or members (e.g., one unit to house processor 95 and memory 96 and a separate unit to house interrogator 87 and receiver 98) that are coupled to one another.

During operations, tension is selectively applied to legs 82', 82" of tendon 82 via actuators 87, 89 to deflect distal tip 50 of surgical cannula 10 in a desired direction. Specifically, if tension is applied to leg 82' via actuator 87, distal tip 50 is deflected in a first direction 88 shown in FIG. 17, and if tension is applied to leg 82" via actuator 89, distal tip 50 is deflected in a second direction 83 shown in FIG. 17. As tension is applied to legs 82', 82", the tension is transferred to filters 91 via adhesive 90. Accordingly, tension applied to legs 82', 82" causes a strain in reflectors 91 via adhesive 90. In addition, during these operations, interrogator 97 may emit light signals that are directed to filters 91 via fiber optic lines 92, and these light signals are then reflected back to controller 94 (particularly to receiver 98) by reflectors 91. Generally speaking, when a strain is applied to filters 91 (e.g., a strain resulting from the tension in legs 82', 82"), the reflected light signals may have an altered wavelength response that is characteristic of the strain experienced by the filter 91. As a result, machine readable instructions stored on member 96 and carried out by processor 95 may analyze the reflected light signals received by receiver 98 and calculate a strain experienced by filter 91 and ultimately to tension applied to legs 82', 82" at filter 91. Thus, controller 94 may actively monitor the strain placed across filter 91 and thus also the force or tension applied to legs 82', 82" of tendon 82 during operations.

Without being limited to this or any other theory, because the tension in legs 82', 82" is measured, via reflector 91, at a point relatively close to distal tip 50 (e.g., at the location of adhesive 90), friction generated by engagement of legs 82', 82" and other objects or components between distal tip 50 and the proximal end of surgical cannula 10 is not measured by controller 94. Therefore, the force or tension measurements taken by controller 94 for tendon 82 may be free of any noise generated by friction applied along legs 82', 82" such that the accuracy of these force or tension measurements may be increased.

Referring still to FIG. 17, in some embodiments tendon 82 (see FIGS. 11 and 12) may comprise fiber optic lines (e.g., fiber optic lines 92). Thus, in these embodiments, legs 82', 82" are coupled to both actuators 87, 89 and controller 94 (particularly interrogator 97 and receiver 98). During operation, tension is applied to legs 82', 82" via actuators 87, 89, respectively, as previously described. In addition, light signals are also simultaneously passed through legs 82', 82" and reflectors 91 to facilitate the tension measurements previously described above.

While embodiments of surgical cannula 10 discussed above have included a hinge 20 having a plurality of first segments 22 and a second segment 30, in other embodiments, the hinge 20 may include a fewer number of components. For instance, referring now to FIG. 18, another embodiment of surgical cannula 400 is shown. Surgical cannula 400 is substantially the same as surgical cannula 10 shown in FIG. 1, and thus, components of surgical cannula 400 that are shared with cannula 10 are identified with the same reference numerals, and the discussion below will focus on the features of cannula 400 that are different form cannula 10.

Figure 18:
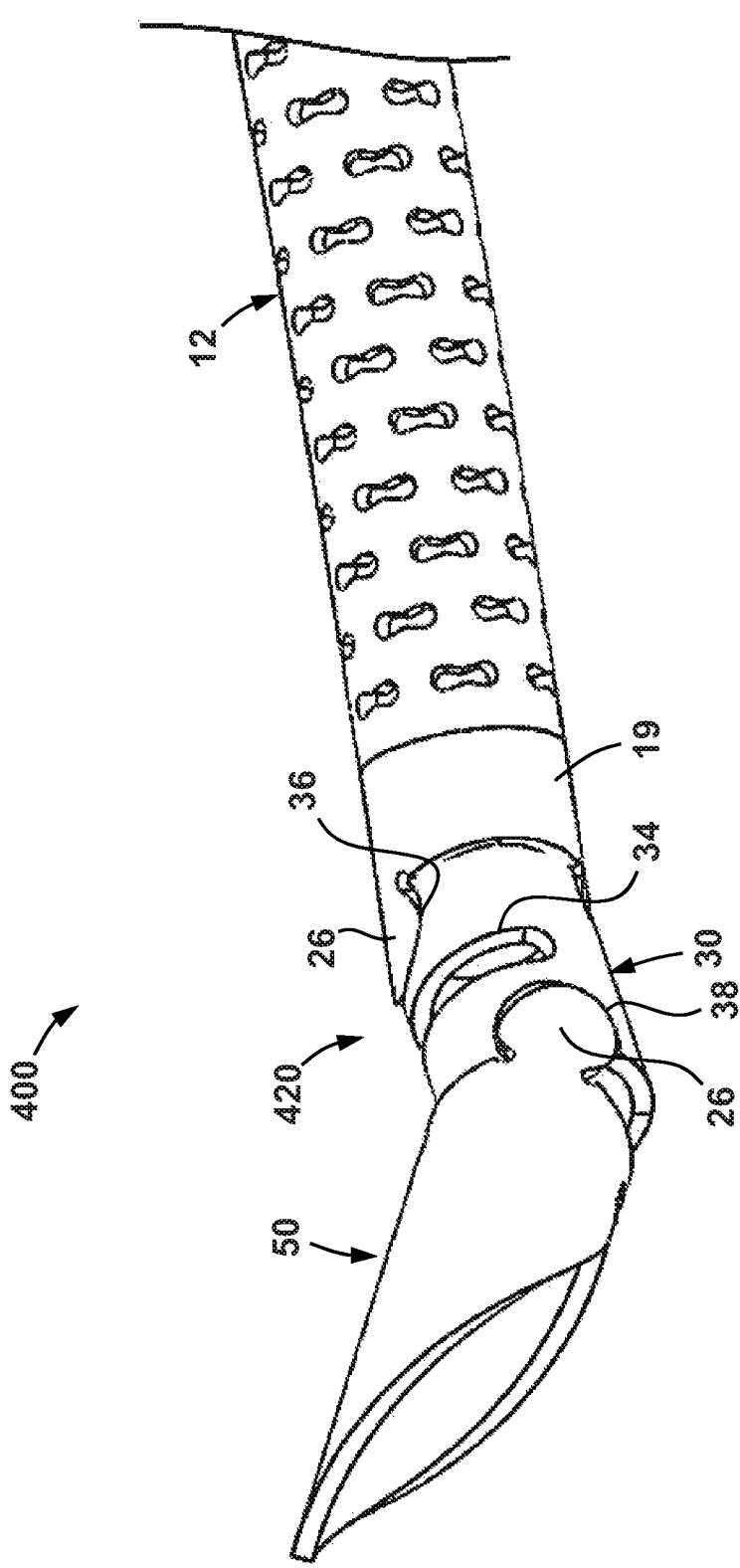
FIG. 18 is a perspective view of another surgical cannula according to some embodiments.

In particular, surgical cannula 400 includes tubular body 12, distal tip 50, and a hinge 420. Hinge 420 does not include the first segments 22 (e.g., segments 22A, 22B, 22C in FIG. 1) and instead only includes second segment 30, which is the same as previously described above. As shown in FIG. 18, pins 26 of connector 19 on tubular body 12 are pivotably disposed within first sockets 36 of segment 30, and pins 26 of distal tip 50 are pivotably disposed within second sockets 38 of segment 30. Thus, during operations, distal tip 50 may be pivoted within a first longitudinal plane due to relative pivoting between segment 30 and connector 19, and may be pivoted within a second longitudinal plane, that is orthogonal to the first longitudinal plane, due to relative pivoting between distal tip 50 and segment 30. Tendons (e.g., such as tendons 80, 82, previously described) may be coupled to surgical cannula 400 to as to deform hinge 420 and deflect distal tip 50 in substantially the same manner as previously described above. Accordingly, a detailed description of these operations is omitted in the interests of brevity.

As is described above for surgical cannula 10, the components of surgical cannula 400 may be formed in-situ by a laser cutting operation. Thus, surgical cannula 400 may be manufactured by starting with a hollow, elongate cylindrical member and cutting the various lines and apertures with an appropriate cutting tool (e.g., a laser cutting tool as described above) to form the connected distal tip 50, hinge 420, and tubular body 12.

Figure 19:
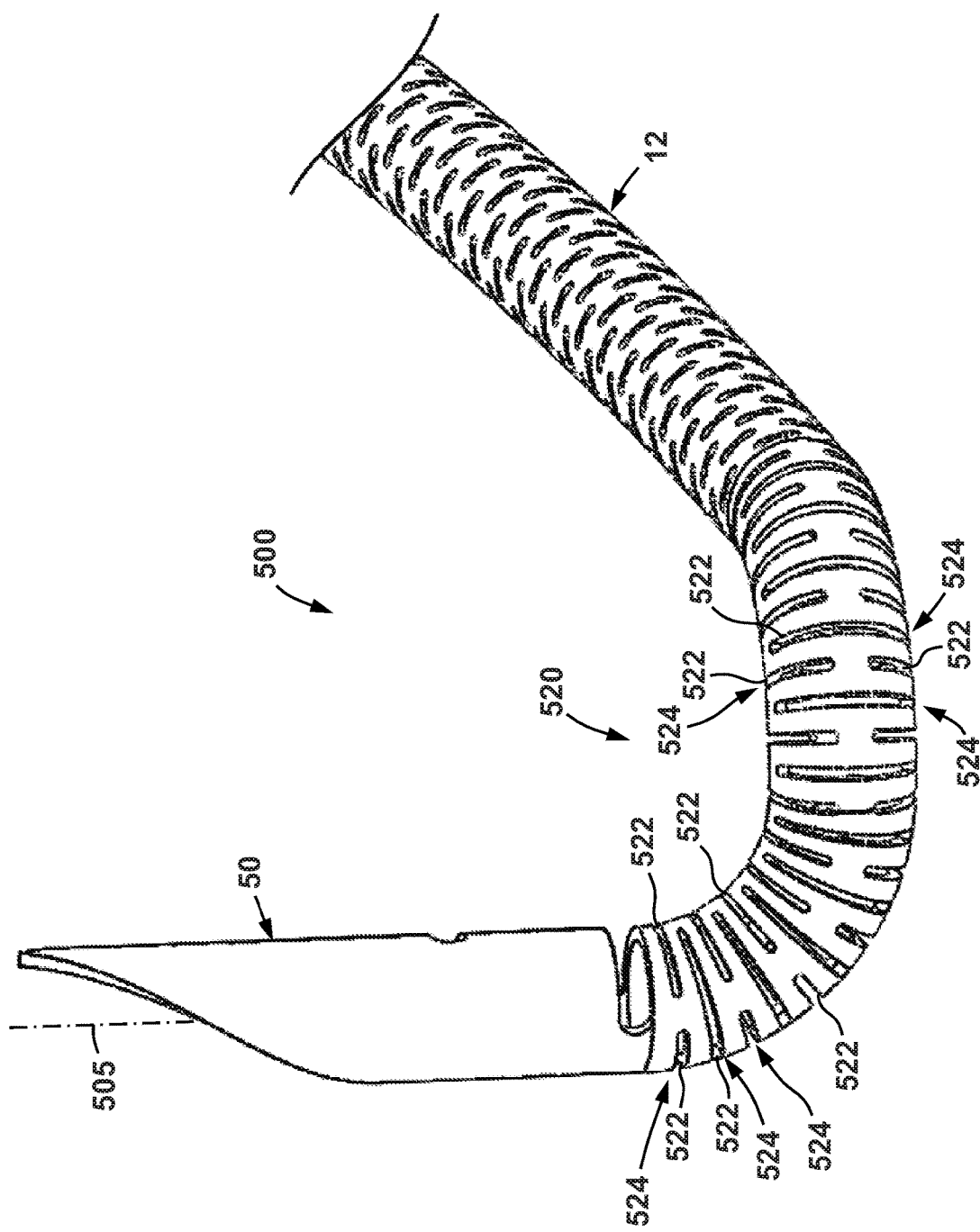
FIG. 19 is a perspective view of another surgical cannula according to some embodiment.

Referring now to FIG. 19, another embodiment of a surgical cannula 500 is shown. Surgical cannula 500 is substantially the same as surgical cannula 10 shown in FIG. 1, and thus, components of surgical cannula 500 that are shared with cannula 10 are identified with the same reference numerals, and the discussion below will focus on the features of cannula 500 that are different form cannula 10.

In particular, surgical cannula 500 includes a central axis 505 tubular body 12, distal tip 50, and a hinge 520. Hinge 520 includes a plurality of circumferential slits or grooves 522 that are configured to provide flexibility to hinge 520 in a plurality of different planes and directions. In this embodiment, grooves 522 extend circumferentially less than 180° about axis 505. In addition, grooves 522 are arranged in a plurality of axially adjacent rows 524 such that each row 524 includes a pair of grooves 522 disposed radially opposite one another across axis 505. In addition, the grooves 522 of each row 524 are circumferentially shifted compared to the orientation of the grooves 522 of the (or each) immediately axially adjacent row 524. Thus, the circumferential ends of each groove 522 are misaligned from each immediately axially adjacent groove 522 along hinge 520. It should be appreciated that the arrangement, spacing, and sizing of grooves 522 may be altered in other embodiments. For instance, in some embodiments, each groove 522 is disposed on a radially opposite side of hinge 520 from the (or each) immediately axially adjacent groove.

During operations, the grooves 522 provide flexibility to hinge 520 along a plurality of directions and planes. Tendons (e.g., such as tendons 80, 82, previously described) may be coupled to surgical cannula 500 to as to deform hinge 520 and deflect distal tip 50 in substantially the same manner as previously described above. Accordingly, a detailed description of these operations is omitted in the interests of brevity.

As is described above for surgical cannula 10, the components of surgical cannula 500 may be formed in-situ by a laser cutting operation. Thus, surgical cannula 500 may be manufactured by starting with a hollow, elongate cylindrical member and cutting the various lines and apertures with an appropriate cutting tool (e.g., a laser cutting tool as described above) to form the connected distal tip 50, hinge 520, and tubular body 12.

Figure 20:
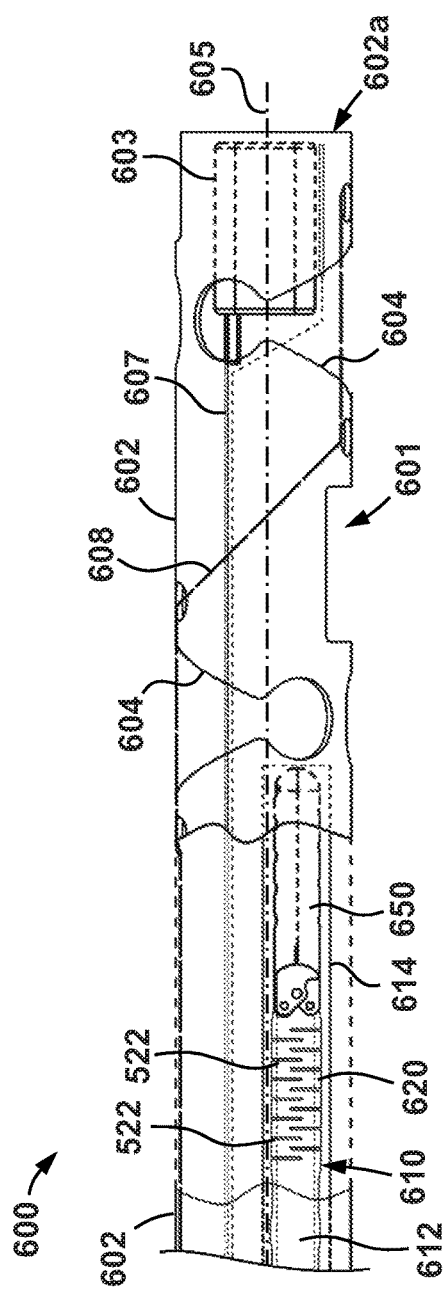
FIGS. 20 and 21 are side views of a surgical instrument according to some embodiments.
Figure 21:
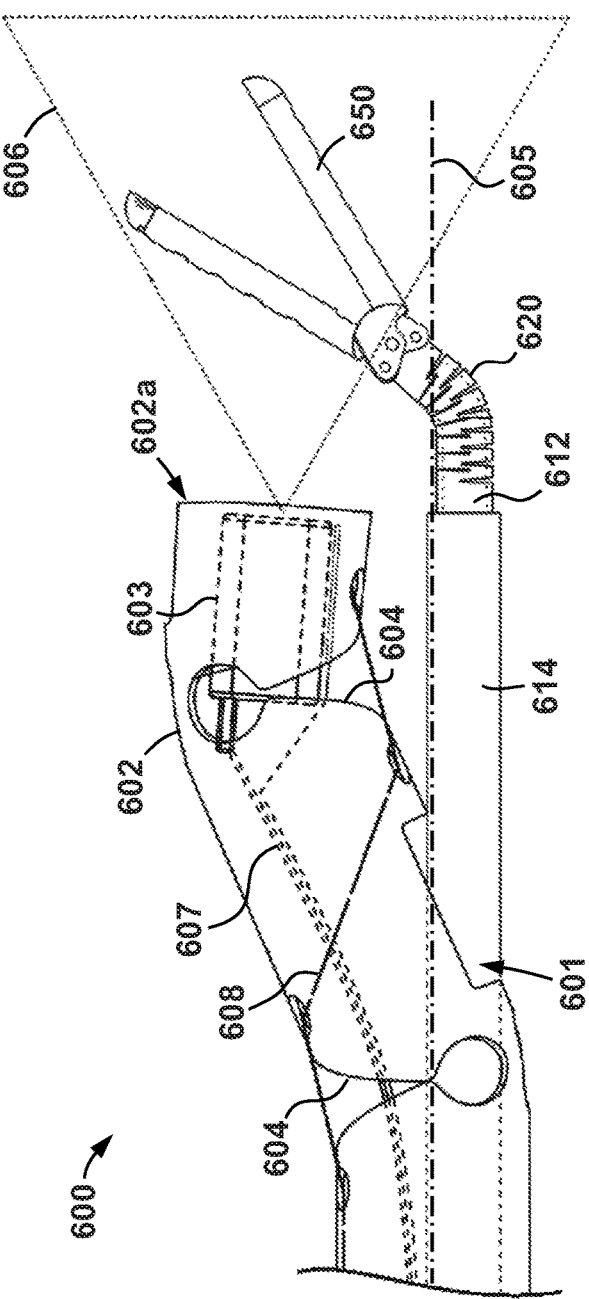

Some embodiments disclosed herein relate to a surgical tools or instruments that include or incorporate embodiments of the steerable surgical cannulas (e.g., surgical cannulas 10, 400, 500, etc.) previously described above. For instance, reference is now made to FIGS. 20 and 21, which show a surgical instrument 600. In this embodiment surgical instrument 600 may be used during an endoscopic procedure. In particular, in this embodiment, surgical instrument may be particularly useful for an endoscopic surgical procedure within a patient's ear.

Surgical instrument 600 includes a central or longitudinal axis 605 and an outer sheath 602 including a plurality of flexure joints 604 and a tool window 601. A camera 603 is mounted within sheath 602 that is configured to capture images or video through an open distal end 602a of sheath 602 during an operation. Camera 603 may include a light source (not shown) coupled thereto or integrated therewith (not shown) to enhance the images captured thereby. One or more conductors 607 are coupled to camera 603 and are routed back through protective sheath 602 to a proximal end (not shown) of surgical instrument 600. Conductors 607 may comprise any conductive member or path configured to transmit power, electrical, light, or other signals between camera 603 and an associated controlling device.

A surgical cannula 610 is retractably disposed within protective sheath 602. Surgical cannula 610 may comprise any of the previously described surgical cannulas (e.g., cannulas 10, 400, 500, etc.) or components thereof. Thus, components of surgical cannula 610 that are shared with component of the previously disclosed surgical cannulas 10, 400, 500 are identified with the same reference numerals. In this embodiment, surgical cannula 610 includes tubular body 12 (which may or may not include apertures 14 as previously described), a hinge 620, and a distal tip 650. In this embodiment, hinge 620 includes grooves 622 that are similar to the grooves 522 described above for surgical cannula 500. In addition, distal tip 50 comprises a pair of surgical forceps for grasping tissue, or other objects or devices during a surgical procedure. Surgical cannula 610 is retractably inserted within a tubular jacket or sheath 614 which is further disposed within protective sheath 602.

A tendon 608, which may be similar to tendons 80, 82 previously described above, is secured to protective sheath 602 and is routed back along sheath 602 toward its proximal end (not shown). During operations, tension may be applied to tendon 608 (e.g., directly by an operator or through an actuator, etc.) so as to deflect distal end 602a of sheath 602, thereby allowing surgical cannula 610 to extend axially from tubular jacket 614 and through tool window 601 such that a surgical procedure (or portion thereof) may be performed with distal tip 650. During these operations, camera 603 may capture images of the distal tip 650 within a field of view 606, so that the physician may monitor the progress of the surgical procedure.

In addition, during the above described operations, distal tip 650 of cannula 610 may be deflected and steered by selectively applying tension to tendons mounted thereto (not shown—see e.g., tendons 80, 82 in FIGS. 11, 12, 14, 15, etc.) in the same manner as described above. Thus, a detailed description of these operations with respect to surgical cannula 610 is omitted herein in the interest of brevity.

Figure 22:
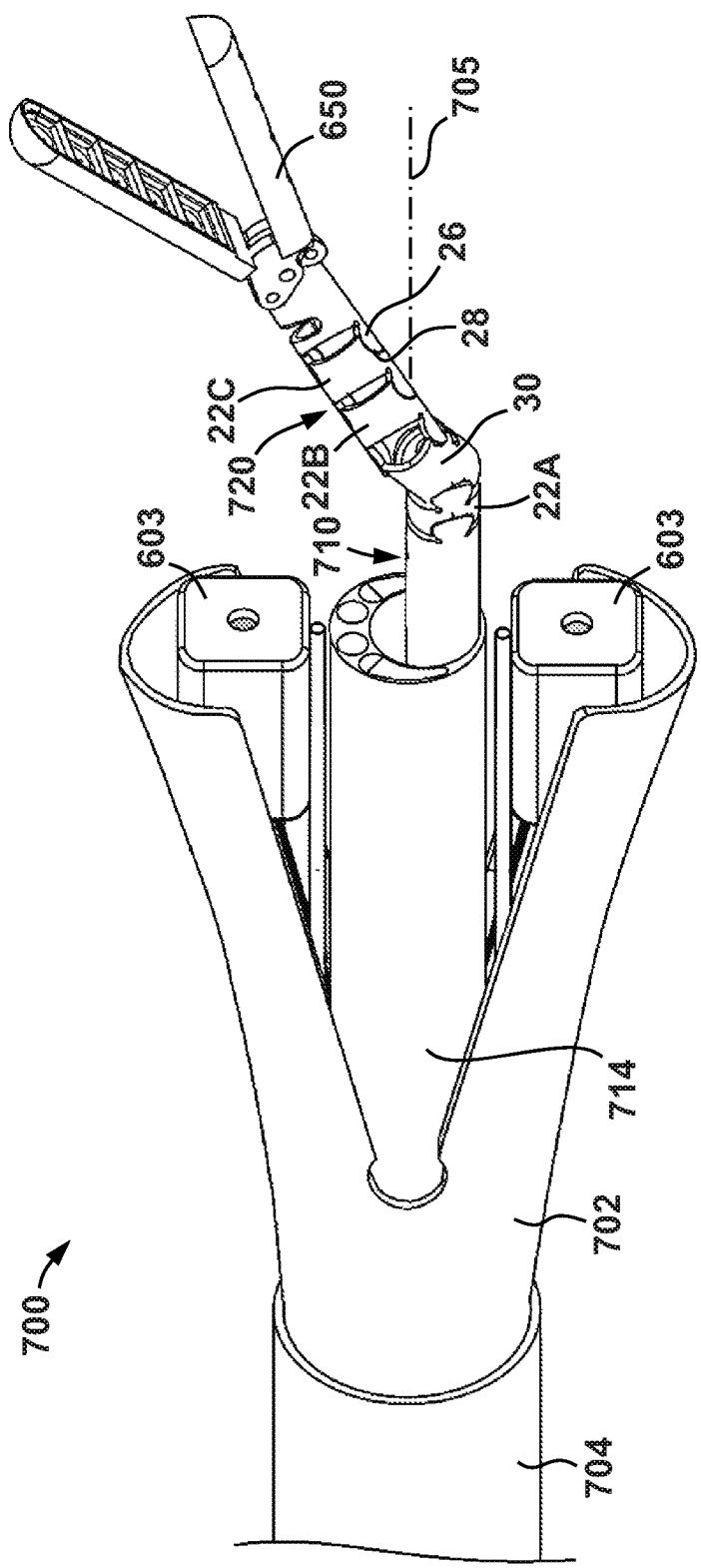
FIG. 22 is a side view of another surgical instrument according to some embodiments.

Referring now to FIG. 22, another surgical instrument 700 is shown. In this embodiment, like surgical instrument 600, surgical instrument 700 may also be particularly useful for an endoscopic surgical procedure within a patient's ear.

Surgical instrument may include a central axis 705, an outer tube 704, a split tube 702 concentrically disposed within outer tube 704, a tool channel 714 concentrically disposed within split tube 702, and a surgical cannula 710 retractably disposed within tool channel 714.

Surgical cannula 710 may comprise any of the previously described surgical cannulas (e.g., cannulas 10, 400, 500, 610, etc.) or components thereof. Thus, any of the components of surgical cannula 710 that are shared with components of the previously disclosed surgical cannulas 10, 400, 500, 610 are identified with the same reference numerals. In this embodiment, surgical cannula 710 includes tubular body 12 (which may or may not include apertures 14 as previously described), a hinge 720, and a distal tip 750. Hinge 720 is substantially the same as hinge 20 shown in FIG. 1, and thus includes segments 22A, 22B, 22C, and 30, the relative arrangement thereof being the same as previously described above for hinge 20. In addition, distal tip 750 includes a pair of pins 26 that are pivotably disposed within the socket 28 of segment 22C in the same manner as described above for distal tip 50. Further, like distal tip 650, in this embodiment distal tip 750 comprises a pair of surgical forceps.

During operations, split tube 702, tool channel 614, and surgical cannula 710 may all be retracted axially within outer tube 702 (e.g., such as when surgical instrument 700 is being inserted within the body of the patient). When desired, split tube 702, tool channel 614, and surgical cannula 710 may be axially projected from outer tub 704 such that split tube 702 opens to thereby expose tool channel 714. Thereafter, surgical cannula 710 may be projected from tool channel 714 such that a surgical procedure (or portion thereof) may be performed with distal tip 750. During these operations, cameras 603 (which are the same as camera 603 described above for surgical instrument 600) may capture images of the distal tip 750, so that the physician may monitor the progress of the surgical procedure. Cameras 603 are mounted within split tube 702 and are moved radially outward form central axis 705 when split tube 702 opens to expose tool channel 714 and surgical cannula 710 during operations.

In addition, during the above described operations, distal tip 750 of cannula 710 may be deflected and steered by selectively applying tension to tendons mounted thereto (not shown—see e.g., tendons 80, 82 in FIGS. 11, 12, 14, 15, etc.) in the same manner as described above. Thus, a detailed description of these operations with respect to surgical cannula 710 is omitted herein in the interest of brevity.

Embodiments disclosed herein have included various improvements to a surgical cannula (e.g., a steerable surgical cannula). For instance, some embodiments disclosed herein have included surgical cannulas (e.g., surgical cannulas 10, 400, 500, 610, 710, etc.) that include a plurality of patterned holes or apertures (e.g., apertures 14, 100, 200, 300, etc.) therein to enhance axial bending or deformation, while maintaining sufficient torsional rigidity to facilitate steering of the cannula during operations. In addition, some embodiments of the cannulas disclosed herein have include a deformable hinge that may be formed in situ from a solid tubular member so as to avoid the tedious and potentially damaging assembly process described above (e.g., hinges 20, 420, 520, 620, 720, etc.). Further, some embodiments disclosed herein have included force sensing tendons (e.g., tendons 80, 82, etc.) for deflecting or deforming the tip of the cannula during operations that may allow the physician or operator (or robotic surgical device) to actively and accurately monitor the force or tension loads placed on the tendons during operations. Thus, through use of the embodiments disclosed herein, surgical operations utilizing a steerable cannula (e.g., such as surgical procedures carried out by a robotic surgical device) may be enhanced and improved.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A surgical cannula, comprising:
   a tubular body;
   a distal tip coupled to the tubular body;
   a tendon at least partially positioned external and radially outside the tubular body, wherein the tendon is coupled to the distal tip, and wherein application of a tension to the tendon is configured to displace the distal tip;
   a fiber brag grating (FBG) reflector mounted to the tendon such that a tension in the tendon causes a strain on the FBG reflector;
   a controller coupled to the FBG reflector with a fiber optic line, wherein the controller is configured to receive reflected light from the FBG reflector and to determine the tension in the tendon based on the received reflected light; and
   a sheathing disposed about the tubular body, wherein the sheathing defines a channel extending along the tubular body, and wherein the tendon and the fiber optic line extend through the channel.

2. The surgical cannula of claim 1, wherein the tendon comprises poly-paraphenylene terephthalamide.

3. The surgical cannula of claim 1, wherein the FBG reflector comprises a polarization maintaining FBG reflector.

4. The surgical cannula of claim 1, wherein the tendon comprises a fiber optic line, and wherein the controller is coupled to the FBG reflector with the tendon.

5. A surgical cannula, comprising:
   a tubular body;
   a distal tip coupled to the tubular body;
   a tendon at least partially positioned external and radially outside the tubular body, wherein the tendon is coupled to the distal tip, and wherein application of a tension to the tendon is configured to displace the distal tip;
   a fiber brag grating (FBG) reflector mounted to the tendon such that a tension in the tendon causes a strain on the FBG reflector;
   a controller coupled to the FBG reflector, wherein the controller is configured to receive reflected light from the FBG reflector and to determine the tension in the tendon based on the received reflected light; and
   a sheathing disposed about the tubular body, wherein the sheathing defines a channel extending along the tubular body, and wherein the tendon extends through the channel.

6. A surgical cannula, comprising:
   a central axis;
   a tubular body;
   a distal tip coupled to the tubular body such that the distal tip is configured to deflect relative to the tubular body;
   a hinge axially disposed between the tubular body and the distal tip, wherein the hinge comprises a plurality of axially adjacent segments pivotably coupled to one another, wherein the hinge is pivotably coupled to the tubular body and to the distal tip, wherein one of the plurality of axially adjacent segments comprises:
      a body having a radially outer surface and a radially inner surface defining a throughbore extending axially through the body; and
      a slot extending radially through the body from the radially outer surface to the throughbore;
   a tendon seated in the slot of the hinge, wherein application of a tension to the tendon is configured to displace the distal tip;
   a plurality of apertures extending through the tubular body, wherein each of the apertures comprises:
      a first end and a second end circumferentially spaced from the first end;
      a first curved surface at the first end;
      a second curved surface at the second end;
      a first pair of straight edges extending from the first curved surface;
      a second pair of straight edges extending from the second curved surface,
      wherein a first edge of the first pair of straight edges intersects a first edge of the second pair of edges at a first point;
      wherein a second edge of the first pair of straight edges intersects a second edge of the second pair of edges at a second point;
      wherein the first pair of edges converge toward one another when moving from the first curved surface to the first and second points; and
      wherein the second pair of edges converge toward one another when moving from the second curved surface toward the first and second points.

7. The surgical cannula of claim 6, wherein the plurality of apertures are arranged into a plurality of axially spaced rows, wherein each of the plurality of axially spaced rows comprises more than one of the plurality of apertures.

8. The surgical cannula of claim 7, wherein the apertures within each axially spaced row are uniformly, circumferentially spaced about the central axis.

9. The surgical cannula of claim 8, wherein the apertures in each of the axially spaced rows are circumferentially shifted from the apertures in each of the immediately axially adjacent rows.

* * * * *